United States Patent [19]

Heitsch et al.

[11] Patent Number: 5,468,764
[45] Date of Patent: Nov. 21, 1995

[54] ANGIOTENSIN II RECEPTOR ANTAGONISTS FOR THE TREATMENT OF DISTURBANCES IN CARDIAC RHYTHM

[75] Inventors: Holger Heitsch, Hofheim am Taunus; Wolfgang Linz, Mainz; Adalbert Wagner, Hattersheim am Main; Heinz-Werner Kleemann, Bad Homburg, all of Germany

[73] Assignee: Hoechst Aktiengesellschaft, Frankfurt am Main, Germany

[21] Appl. No.: 83,337

[22] Filed: Jun. 29, 1993

[30] Foreign Application Priority Data

Jul. 1, 1992 [DE] Germany ............... 42 21 536.6
Aug. 27, 1992 [DE] Germany ............... 42 28 554.2

[51] Int. Cl.⁶ .................................. A61K 31/41
[52] U.S. Cl. .................... 514/382; 514/385; 514/387
[58] Field of Search ................... 514/821, 382, 514/385, 387

[56] References Cited

U.S. PATENT DOCUMENTS

| 4,443,456 | 4/1984 | Douglas et al. ............... 514/821 |
| 4,880,804 | 11/1989 | Carini et al. ............... 514/234.5 |
| 5,032,604 | 7/1991 | Baldwin et al. ............... 514/821 |
| 5,276,034 | 1/1994 | Pascal et al. ............... 514/821 |
| 5,326,774 | 7/1994 | Mashovsky et al. ............... 514/821 |

FOREIGN PATENT DOCUMENTS

| 253310 | 1/1988 | European Pat. Off. ............... 514/821 |
| 324377 | 7/1989 | European Pat. Off. ............... 514/821 |
| 399732 | 11/1990 | European Pat. Off. ............... 514/821 |
| 399731 | 11/1990 | European Pat. Off. ............... 514/821 |
| 401030 | 12/1990 | European Pat. Off. ............... 514/821 |
| 400835 | 12/1990 | European Pat. Off. ............... 514/821 |

Primary Examiner—James H. Reamer
Attorney, Agent, or Firm—Finnegan, Henderson, Farabow, Garrett & Dunner

[57] ABSTRACT

Angiotensin II receptor antagonists for the treatment of disturbances in cardiac rhythm.

Antagonists for angiotensin II receptors of the AT, subtype can be employed for combating cardiac arrhythmias, using azole derivatives.

6 Claims, No Drawings

ANGIOTENSIN II RECEPTOR ANTAGONISTS FOR THE TREATMENT OF DISTURBANCES IN CARDIAC RHYTHM

DESCRIPTION

The present invention relates to antagonists for angiotensin II receptors of the $AT_1$ sub-type for use as medicines for the therapy of disturbances in cardiac rhythm.

Imidazole-fused aromatic compounds are known inter alia from EP-A 399 731, EP-A 399 732, EP-A 400 835 and EP-A 434 038 as antagonists of angiotensin II receptors. Imidazole derivatives and their use as antagonists of angiotensin II receptors are known from EP-A 28 834, EP-A 253 310, EP-A 401 030 and EP-A 324 377.

The present invention relates quite generally to the use of antagonists for angiotensin II receptors of the $AT_1$ sub-type for combating disturbances in cardiac rhythm. These specific $AT_1$ receptors are described in respect of nomenclature and characteristics by, for example, F. M. Bumpus et al. in Hypertension 17 (1991), pages 720 to 721.

Compounds of the formulae (I), (II), (III) and (IV), the structure and preparation of which are explained below, are particularly suitable as antagonists for this receptor sub-type. Because of their metabolization, these compounds have proven to be particularly advantageous in humans.

The invention thus relates to the use of compounds of the formula (I)

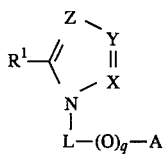
(I)

in which the symbols have the following meaning:
a) X, Y and Z are identical or different and are N or $CR^2$;
b) $R^1$ is
1. $(C_1-C_{10})$-alkyl,
2. $(C_3-C_{10})$-alkenyl,
3. $(C_3-C_{10})$-alkynyl,
4. $-OR^3$,
5. $(C_3-C_8)$-cycloalkyl,
6. $(C_4-C_{10})$-cycloalkylalkyl,
7. $(C_5-C_{10})$-cycloalkylalkenyl,
8. $(C_5-C_{10})$-cycloalkylalkynyl,
9. $-(CH_2)_m-B-(CH_2)_n-R^4$,
10. -benzyl
11. a radical as defined under b) 1., 2., 3. or 9. which is monosubstituted by $CO_2R^3$,
12. a radical as defined under b) 1., 2., 3. or 9. in which 1 to all the H atoms are replaced by fluorine or
13. the radical defined under b) 10., which is substituted on the phenyl by 1 or 2 identical or different radicals from the series comprising halogen, $(C_1-C_4)$-alkoxy and nitro;
c) $R^2$ is
1. hydrogen,
2. halogen,
3. nitro,
4. $C_vF_{2v+1}$,
5. pentafluorophenyl,
6. cyano,
7. $-O-R^6$,
8. phenyl,
9. phenyl-$(C_1-C_3)$-alkyl,
10. $(C_1-C_{10})$-alkyl,
11. $(C_3-C_{10})$-alkenyl,
12. phenyl-$(C_2-C_6)$-alkenyl,
13. 1-imidazolyl-$(CH_2)_m-$,
14. 1,2,3-triazolyl-$(CH_2)_n-$,
15. tetrazolyl-$(CH_2)_m-$,
16. $-(CH_2)_{o-1}-CHR^7-OR^5$,
17. $-(CH_2)_o-O-CO-R^3$,
18. $-(CH_2)_o-S-R^6$,
19. $-S(O)_r-R^{19}$,
20. $-CH=CH-(CH_2)_m-CHR^3-OR^6$,
21. $-CH_2=CH-(CH_2)_m-CO-R^8$,
22. $-CO-R^8$,
23. $-CH=CH-(CH_2)_m-O-CO-R^7$,
24. $-(CH_2)_m-CH(CH_3)-CO-R^8$,
25. $-(CH_2)_o-CO-R^8$, 26. 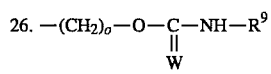

27. 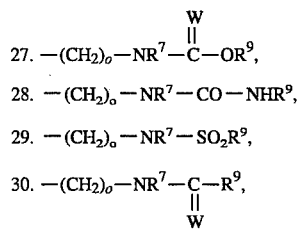

28. $-(CH_2)_o-NR^7-CO-NHR^9$,

29. $-(CH_2)_o-NR^7-SO_2R^9$,

30.

31. $-(CH_2)_nF$,
32. $-(CH_2)_n-O-NO_2$,
33. $-CH_2-N_3$,
34. $-(CH_2)_n-NO_2$,
35. $-CH=N-NR^5R^7$,
36. phthalimido-$(CH_2)_n-$, 37. 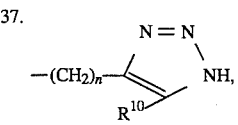

38. 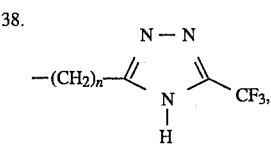

39. 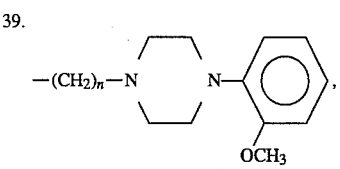

40. 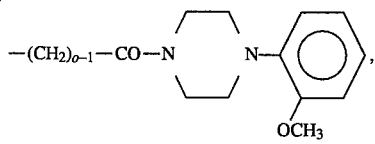

41. phenyl-$SO_2$—NH—N=CH—,

42. 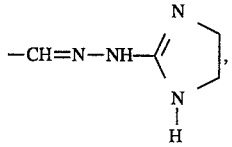

43. —$(CH_2)_n$—$SO_2$—$NR^7$—CS—$NR^6R^9$,
44. —$(CH_2)_nSO_2$—$NR^7$—CO—$NR^6R^9$,
45. —$(CH_2)_o$—$SO_2R^9$,
46. a radical as defined under c) 8. or 9., which is substituted on the phenyl by 1 or 2 identical or different radicals from the series comprising halogen, hydroxyl, methoxy, trifluoromethyl, $CO_2R^3$ and phenyl,
47. a radical as defined under c) 10., 11 or 19. in which one to all the H atoms are replaced by fluorine,
48. the radical defined under c) 14., which is substituted by 1 or 2 identical or different radicals from the series comprising methoxycarbonyl and $(C_1-C_4)$-alkyl,
49. —$(CH_2)_n$—$SO_2$—$NR^7$—CO—$R^6$ or
50. —$(CH_2)_n$—$SO_2$—$NR^7CS$—$R^6$;

d) $R^3$ is
  1. hydrogen,
  2. $(C_1-C_8)$-alkyl,
  3. $(C_3-C_8)$-cycloalkyl,
  4. phenyl,
  5. benzyl or
  6. the radical defined under d) 2. in which 1 to all the H atoms are replaced by fluorine;

e) $R^4$ is
  1. hydrogen,
  2. $(C_1-C_6)$-alkyl,
  3. $(C_3-C_8)$-cycloalkyl,
  4. $(C_2-C_4)$-alkenyl or
  5. $(C_2-C_4)$-alkynyl;

f) $R^5$ is
  1. hydrogen,
  2. $(C_1-C_6)$-alkyl,
  3. $(C_3-C_8)$-cycloalkyl,
  4. phenyl or
  5. benzyl;

g) $R^6$ and $R^9$ are identical or different and are
  1. hydrogen,
  2. $(C_1-C_6)$-alkyl, which can be substituted by 1 to 3 radicals from the series comprising $(C_1-C_6)$-alkoxy, which can be substituted in turn by 1–3 radicals from the series comprising hydroxyl, $(C_1-C_6)$-alkoxy, amino, mono-$(C_1-C_6)$-alkylamino and di-$(C_1-C_6)$-alkylamino, $(C_2-C_{10})$-alkenyl, hydroxyl, amino, mono-$(C_1-C_6)$-alkylamino, di-$(C_1-C_6)$-alkylamino, $(C_1-C_6)$-alkoxycarbonylamino, $(C_6-C_{12})$-aryl-$(C_1-C_4)$-alkoxycarbonylamino, $(C_6-C_{10})$-aryl, $(C_6-C_{10})$-aryl-$(C_1-C_3)$-alkyl, $(C_1-C_9)$-heteroaryl, carboxyl and $(C_1-C_4)$-alkoxycarbonyl,
  3. $(C_3-C_8)$-cycloalkyl, in which the cycloalkyl part can be further substituted by 1–3 radicals from the series comprising $(C_1-C_4)$-alkyl and $(C_2-C_4)$-alkenyl,
  4. $(C_3-C_8)$-cycloalkyl-$(C_1-C_3)$-alkyl,
  5. $(C_6-C_{12})$-aryl, preferably phenyl,
  6. $(C_6-C_{10})$-aryl-$(C_1-C_4)$-alkyl,
  7. $(C_1-C_9)$-heteroaryl, which can be partly or completely hydrogenated,
  8. a radical as defined under g) 5., 6., 7., 9., 15., 16., 17., 19., 20. or 21., which is substituted by one or two identical or different radicals from the series comprising halogen, hydroxyl, $(C_1-C_4)$-alkyl, methoxy, nitro, cyano, $CO_2R^3$, trifluoromethyl, $NR^{11}R^{12}$ and

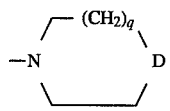

9. $(C_1-C_9)$-heteroaryl-$(C_1-C_3)$-alkyl, in which the heteroaryl part can be partly or completely hydrogenated,
  10. $(C_1-C_6)$-alkyl, in which 1 to all the H atoms are replaced by fluorine,
  11. $(C_2-C_{10})$-alkenyl, $(C_2-C_{10})$-alkenoyl or $(C_2-C_{10})$-alkadienyl,
  12. $(C_3-C_8)$-cycloalkenyl,
  13. $(C_3-C_8)$-cycloalkenyl-$(C_1-C_3)$-alkyl,
  14. bi- or tricyclic $(C_4-C_{10})$-cycloalkenyl-$(C_1-C_4)$-alkyl, which can be further substituted by 1–3 $(C_1-C_4)$-alkyl radicals,
  15. $(C_6-C_{10})$-aryl-$(C_1-C_4)$-alkyl,
  16. $(C_6-C_{10})$-aryl-$(C_3-C_6)$-alkenyl,
  17. $(C_1-C_9)$-hetaryl-$(C_3-C_6)$-alkenyl,
  18. $(C_3-C_6)$-alkynyl,
  19. $(C_6-C_{10})$-aryl-$(C_3-C_6)$-alkynyl,
  20. $(C_1-C_9)$-hetaryl-$(C_3-C_6)$-alkynyl or
  21. $R^6$ and $R^9$, together with the N atom carrying them, are a hetaryl, which can also be partly or completely hydrogenated;

h) $R^7$ is
  1. hydrogen,
  2. $(C_1-C_6)$-alkyl,
  3. $(C_3-C_8)$-cycloalkyl,
  4. $(C_6-C_{12})$-aryl-$(C_1-C_6)$-alkyl, preferably benzyl,
  5. phenyl or
  6. $(C_1-C_9)$-heteroaryl;

i) $R^8$ is
  1. hydrogen
  2. $(C_1-C_6)$-alkyl
  3. $(C_3-C_8)$-cycloalkyl
  4. phenyl-$(CH_2)_q$—,
  5. $OR^6$,
  6. $NR^{11}R^{12}$ or 7. 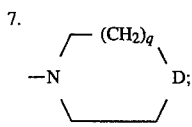

j) $R^{10}$ is cyano, nitro or $CO_2R^7$;
k) $R^{11}$ and $R^{12}$ are identical or different and are
  1. hydrogen,
  2. $(C_1-C_4)$-alkyl,
  3. phenyl,
  4. benzyl or
  5. α-methylbenzyl;
l) D is $NR^{13}$, O or $CH_2$;
m) $R^{13}$ is hydrogen, $(C_1-C_4)$-alkyl or phenyl;
n) A is a biphenyl radical, which can be substituted by up to 4, preferably up to 2, identical or different radicals $R^{14}$ or $R^{15}$;
o) $R^{14}$ is
  1. halogen,
  2. nitroso,
  3. nitro,
  4. amino,
  5. cyano,
  6. hydroxy,
  7. $(C_1-C_6)$-alkyl,
  8. $(C_1-C_4)$-alkanoyl,
  9. $(C_1-C_4)$-alkanoyloxy,
  10. $CO_2R^3$,
  11. methanesulfonylamino,
  12. trifluoromethanesulfonylamino,
  13. —CO—NH—$OR^9$,
  14. —$SO_2$—$NR^6R^7$,
  15. —$CH_2$—$OR^7$,
  16. $(C_1-C_9)$-heteroaryl-$(CH_2)_q$—, preferably 1-tetrazolyl,
  17. $(C_7-C_{13})$-aroyl, 18. 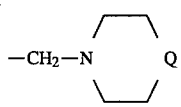

19. 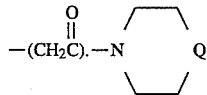

or
  20. $(C_6-C_{12})$-aryl;
p) $R^{15}$ is
  1. hydrogen,
  2. $(C_1-C_6)$-alkyl,
  3. $(C_3-C_8)$-cycloalkyl,
  4. $(C_6-C_{12})$-aryl,
  5. $(C_7-C_{13})$-aroyl,
  6. $(C_1-C_4)$-alkoxy,
  7. $(C_1-C_4)$-alkanoyloxy,
  8. $(C_1-C_9)$-heteroaryl,
  9. $CO_2R^3$,
  10. halogen,
  11. cyano,
  12. nitro,
  13. $NR^6R^7$,
  14. hydroxyl,
  15. —CO—NH—$CHR^5$—$CO_2R^3$,
  16. sulfo,
  17. —$SO_3R^3$,
  18. —$SO_2$—$NR^7$—CO—$NR^6R^9$ or —$SO_2$—$NR^7$—CS—$NR^6R^9$,
  19. —$NR^7$—CO—$NR^6$—$SO_2$—$CH_2$—$R^5$,
  20. —$C(CF_3)_2OH$,
  21. phosphonooxy,
  22. —$PO_3H_2$,
  23. —NH—$PO(OH)_2$,
  24. —$S(O)_rR^6$,
  25. —CO—$R^8$,
  26. —CO—$NR^6R^9$,
  27. —$CR^{20}(OH)$—$PO(OH)_2$,
  28. the radical defined under o) 20., 29. 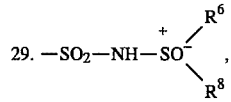

30. 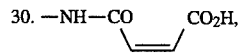

31. 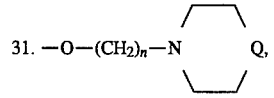

32. 5-tetrazolyl-NH—CO—,
  33. —CO—NH—NH—$SO_2$—$CF_3$,

34. 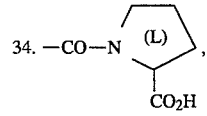

35. 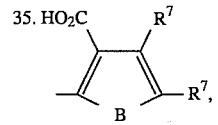

36. 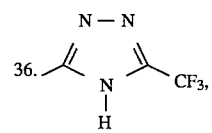

37. 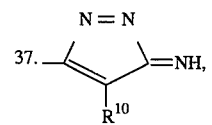

-continued

38. —T—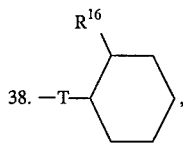,

39. 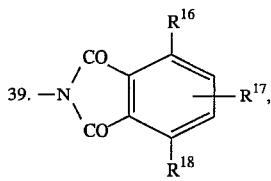,

40. —CO—NH—SO$_2$—R$^{19}$,
41. —SO$_2$—NH—CO—R$^6$ or
42. the radical defined under p) 4., substituted by 1 or 2 identical or different radicals from the series comprising halogen, cyano, nitro, NR$^6$R$^7$ and hydroxyl; or
43. R$^{15}$, together with R$^{14}$, is —CO—NH—SO$_2$,
44. —SO$_2$—NH—CO—O—R$^6$,
45. —SO$_2$—NH—SO$_2$—NR$^6$R$^9$ or
46. —SO$_2$—NH—SO$_2$—R$^6$;

q) B is O, NR$^7$ or S;
r) W is O or S;
s) L is (C$_1$–C$_3$)-alkanediyl;
t) R$^{16}$ is CO$_2$R$^3$ or CH$_2$CO$_2$R$^3$;
u) R$^{17}$ is hydrogen, halogen, (C$_1$–C$_4$)-alkyl or (C$_1$–C$_4$)-alkoxy;
v) R$^{18}$ is hydrogen, (C$_1$–C$_4$)-alkyl or phenyl;
w) R$^{19}$ is
1. (C$_1$–C$_6$)-alkyl,
2. (C$_3$–C$_6$)-cycloalkyl,
3. phenyl,
4. benzyl or
5. the radical defined inder w) 1. in which 1 to all the H atoms are replaced by fluorine;
x) T is
1. a single bond,
2. —CO—,
3. —CH$_2$—,
4. —O—,
5. —S—,
6. —NR$^{21}$—,
7. —CO—NR$^{21}$,
8. NR$^{21}$—CO—,
9. —O—CH$_2$—,
10. —CH$_2$—O—,
11. —S—CH$_2$—,
12. —CH$_2$—S,
13. —NH—CR$^{20}$R$^{22}$,
14. —NR$^{21}$—SO$_2$,
15. SO$_2$—NR$^{21}$—,
16. —CR$^{20}$R$^{22}$—NH,
17. —CH=CH—,
18. —CF=CF—,
19. —CH=CF—,
20. —CF=CH—,
21. —CH$_2$—CH$_2$—,
22. —CF$_2$—CF$_2$—,
23. —CH(OR$^3$)—,
24. —CH(OCOR$^5$)—, 25. 

or

26. 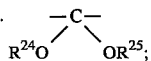;

y) R$^{20}$ and R$^{22}$ are identical or different and are hydrogen, (C$_1$–C$_5$)-alkyl, phenyl, allyl or benzyl;
z) R$^{21}$ is hydrogen, (C$_1$–C$_6$)-alkyl, benzyl or allyl;
a') R$^{23}$ is
1. NR$^{20}$R$^{21}$,
2. ureido,
3. thioureido,
4. toluene-4-sulfonyl or
5. benzenesulfonylamino;
b') R$^{24}$ and R$^{25}$ are identical or different and are (C$_1$–C$_4$)-alkyl, or together are —(CH$_2$)$_q$—;
c') Q is CH$_2$, NH, O or S;
d') m is an integer from 0 to 5;
e') n is an integer from 1 to 5;
f') o is an integer from 1 to 10;
g') q is 0 or 1;
h') r is 0, 1 or 2 and
i') v is an integer from 1 to 6;
and physiologically tolerated salts thereof.

Alkyl, alkenyl and alkynyl can be straight-chain or branched. The same applies to radicals derived therefrom, such as alkanoyl or alkoxy. Cycloalkyl is also understood as meaning alkyl-substituted rings. (C$_6$–C$_{12}$)-Aryl is, for example, phenyl, naphthyl or biphenylyl, preferably phenyl. The same applies to radicals derived therefrom, such as aroyl and aralkyl.

(C$_1$–C$_9$)-heteroaryl is understood as meaning, in particular, radicals which are derived from phenyl or naphthyl, in which one or more CH groups are replaced by N and/or in which at least two adjacent CH groups are replaced by S, NH or O (to form a five-membered aromatic ring). Furthermore, one or both the atoms of the condensation point of bicyclic radicals can also be N atoms (as in indolizinyl).

Heteroaryl is, in particular, furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxylinyl, quinazolinyl or cinnolinyl.

Any stereocenters which occur can be in both the (R) and the (S) configuration.

A is linked via an alkanediyl bridge L, which is preferably a methylene group. The methylene group is preferably bonded directly to the biphenyl radical.

Physiologically tolerated salts of compounds of the formula (I) are understood as meaning both organic and inorganic salts thereof, such as are described in Remington's Pharmaceutical Sciences (17th Edition, page 1418 (1985)). The sodium, potassium, calcium and ammonium salts, inter alia, are preferred for acids groups because of their physical and chemical stability and solubility; the salts of hydrochloric acid, sulfuric acid, phosphoric acid or carboxylic acids or sulfonic acids, such as, for example, acetic acid, citric acid, benzoic acid, maleic acid, fumaric acid, tartaric acid and p-toluenesulfonic acid, inter alia, are preferred for basic groups.

Compounds of the formula (I) which are furthermore preferably employed in the treatment of disturbances in cardiac rhythm are those in which X is N, Y is $CR^2$ and Z is $CR^2$;
X is $CR^2$, Y is N and Z is $CR^2$;
X is $CR^2$, Y is $CR^2$ and Z is N or
X, Y and Z are each N, a) $R^1$ is
1. $(C_1-C_{10})$-alkyl,
2. $(C_3-C_{10})$-alkenyl,
3. $(C_3-C_{10})$-alkynyl,
4. $(C_3-C_8)$-cycloalkyl,
5. benzyl or
6. benzyl, which is substituted as described above (b 13.);

b) $R^2$ is
1. hydrogen,
2. halogen,
3. nitro,
4. $C_vF_{2v+1}$,
5. pentafluorophenyl,
6. cyano,
7. —O—$R^6$,
8. phenyl,
9. phenyl-$(C_1-C_3)$-alkyl,
10. $(C_1-C_{10})$-alkyl,
11. $(C_3-C_{10})$-alkenyl,
12. phenyl-$(C_2-C_6)$-alkenyl,
13. 1-imidazolyl-$(CH_2)_m$—,
14. 1,2,3-triazolyl-$(CH_2)_o$—,
15. tetrazolyl-$(CH_2)_m$—,
16. —$(CH_2)_o$—1—$CHR^7$—$OR^5$,
17. —$(CH_2)_o$—O—$COR^3$,
18. —$COR^8$,
19. —$(CH_2)_o$—(CO—$R^8$
20. —$S(O)_rR^{19}$,
21. —CH=CH—$(CH_2)_m$—$CHR^3$—$OR^6$,
22. —CH=CH—$(CH_2)_m$—CO—$R^8$,
23. —$(CH_2)_o$—NH—CO—$OR^9$,
24. —$(CH_2)_o$—NH—$SO_2$—$R^9$,
25. —$(CH_2)_n$F,
26. —$(CH_2)_o$—$SO_3R^9$,
27. —$(CH_2)_n$—$SO_2$—NH—CO—$NR^6R^9$,
28. —$(CH_2)_n$—$SO_2$—NH—CS—$NR^6R^9$, or
29. a radical as defined under b) 8., 9., 10., 11 or 14., which is substituted as above under c) 46., 47. or 48. in each case as described for such a radical,
30. —$(CH_2)_n$—$SO_2$—$NR^7$—CO—$R^6$ or
31. —$(CH_2)_n$—$SO_2$—$NR^7$—CS—$R^6$;

c) $R^8$ is hydrogen, $(C_1-C_5)$-alkyl, $OR^6$, $NR^{11}R^{12}$ or morpholino;

d) T is
1. a single bond,
2. —CO—,
3. —$CONR^{21}$—,
4. —$CH_2$—$CH_2$—,
5. —$NR^{21}$—CO—,
6. —O—$CH_2$—,
7. —$CH_2$—O—,
8. —S—$CH_2$—,
9. —$CH_2$—S—,
10. —NH—$CH_2$—,
11. —$CH_2$—NH— or
12. —CH=CH— and the other radicals and variables are as defined above.

Particularly preferred compounds of the formula (I) are those in which:

X is N, Y is $CR^2$ and Z is $CR^2$;
X is $CR^2$, Y is N and Z is $CR^2$;
X is $CR^2$, Y is $CR^2$ and Z is N or
X, Y and Z are each N, a) $R^1$ is $(C_1-C_7)$-alkyl, $(C_3-C_{10})$-alkenyl or $(C_3-C_7)$-alkynyl;

b) $R^2$ is
1. chlorine,
2. bromine,
3. $C_vF_{2v+1}$, where v=1, 2 or 3,
4. pentafluorophenyl,
5. O—$R^6$,
6. —$S(O)_rR^{19}$,
7. $(CH_2)_o$—1—$CHR^7$—$OR^5$,
8. $(CH_2)_o$—O—CO—$R^3$,
9. —$COR^8$,
10. —$(CH_2)_o$—CO—$R^8$,
11. —$CH_2$—NH—CO—$R^8$,
12. —$(CH_2)_o$—NH—$SO_2$—$R^9$,
13. —CH=CH—$CHR^3$—$OR^6$,
14. tetrazolyl-$(CH_2)_m$—,
15. —$(CH_2)_n SO_2$—NH—CO—$NR^6R^9$,
16. —$(CH_2)_o$—$SO_3R^9$ or $(C_1-C_6)$-alkyl which is optionally substituted by hydroxyl, preferably hydroxymethyl;

c) $R^3$ is hydrogen, $(C_1-C_4)$-alkyl or benzyl;

d) $R^6$ and $R^9$ are identical or different and are
1. hydrogen,
2. $(C_1-C_6)$-alkyl, which can be substituted by 1 to 3 radicals from the series comprising $(C_1-C_6)$-alkoxy, which can be substituted in turn by 1 to 3 radicals from the series comprising hydroxyl, $(C_1-C_6)$-alkoxy, amino, mono-$(C_1-C_6$ )-alkylamino and di-$(C_1-C_6)$-alkylamino, $(C_2-C_{10})$-alkenyl, hydroxyl, amino, mono-$(C_1-C_6)$-alkylamino, di-$(C_1-C_6)$-alkylamino, $(C_1-C_6)$-alkoxycarbonylamino, $(C_6-C_{12})$-aryl-$(C_1-C_4)$-alkoxycarbonylamino, $(C_6-C_{10})$-aryl, $(C_6-C_{10})$-aryl-$(C_1-C_3)$-alkyl, $(C_1-C_9)$-heteroaryl, carboxyl and $(C_1-C_4)$-alkoxycarbonyl,
3. $(C_3-C_6)$-cycloalkyl,
4. $(C_3-C_6)$-cycloalkyl-$(C_1-C_3)$-alkyl,
5. phenyl,
6. phenyl-$(C_1-C_3)$-alkyl,
7. $(C_1-C_7)$-heteroaryl, which can be partly or completely hydrogenated,
8. a radical as defined above under g) 5., 6., 7. or 9., 14. to 16. and 18. to 20., substituted by 1 or 2 identical or different radicals from the series comprising halogen, hydroxyl, $(C_1-C_4)$-alkyl, methoxy, nitro, cyano, $CO_2R^3$, trifluoromethyl, —$NR^{11}R^{12}$ and

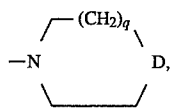

9. $(C_1-C_9)$-heteroaryl-$(C_1-C_3)$-alkyl, in which the heteroaryl part can be partly or completely hydrogenated,
10. $(C_1-C_{10})$-alkyl, in which 1 to all the H atoms are replaced by fluorine,
11. $(C_2-C_4)$-alkenyl or $(C_3-C_6)$-alkenoyl,
12. $(C_3-C_6)$-cycloalkenyl,
13. $(C_3-C_6)$-cycloalkenyl-$(C_1-C_3)$-alkyl,
14. bi- or tricyclic $(C_4-C_{10})$-cycloalkenyl-$(C_1-C_{10})$-alkyl, which can also be substituted by 1 to 3 $(C_1-C_4)$-alkyl radicals,
15. $(C_6-C_{10})$-aryl-$(C_1-C_3)$-alkyl,
16. $(C_6-C_{10})$-aryl-$(C_3-C_6)$-alkenyl,
17. $(C_1-C_6)$-hetaryl-$(C_3-C_6)$-alkenyl,
18. $(C_3-C_6)$-alkynyl,
19. $(C_6-C_{10})$-aryl-$(C_3-C_6)$-alkynyl,
20. $(C_1-C_6)$-hetaryl-$(C_3-C_6)$-alkynyl or
21. $R^6$ and $R^9$, together with the N atom carrying them, are a hetaryl, which can also be partly or completely hydrogenated;

e) $R^7$ is hydrogen, $(C_1-C_4)$-alkyl, $(C_1-C_9)$-heteroaryl or $(C_6-C_{12})$-aryl-$(C_1-C_4)$-alkyl;

f) $R^{14}$ is
1. $(C_1-C_4)$-alkyl,
2. $(C_1-C_4)$-alkoxy,
3. cyano,
4. amino,
5. nitroso,
6. nitro,
7. fluorine,
8. chlorine,
9. bromine,
10. $(C_1-C_9)$-heteroaryl-$CH_2$—,
11. $(C_1-C_4)$-alkanoyloxy,
12. $(C_1-C_4)$-alkanoyl,
13. benzoyl,
14. —NH—CO—$R^7$ or
15. tetrazolyl;

h) $R^{15}$ is
1. $(C_1-C_4)$-alkyl,
2. $(C_6-C_{12})$-aryl,
3. $(C_1-C_3)$-alkanoyloxy,
4. $(C_1-C_4)$-alkoxy,
5. $(C_1-C_9)$-heteroaryl, preferably 5-tetrazolyl,
6. cyano,
7. nitro,
8. hydroxyl,
9. —S(O)$_r R^6$,
10. —SO$_3 R^3$,
11. chlorine,
12. bromine,
13. benzoyl,
14. —CO$_2 R^3$,
15. —CO—NH—$R^6$,
16. —CO—$R^8$,
17. —SO$_2$—NR$^6 R^7$,
18. —SO$_2$—NH—CO—NR$^6 R^9$,
19. —PO$_3 H_2$,
20. —CO—CHR$^5$—CO$_2$H,
21. —NH—CO—NH—SO$_2$—CH$_2$—$R^5$,
22. 5-tetrazolyl—NH—CO—,

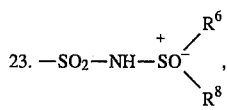

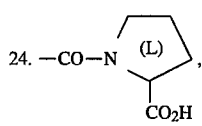

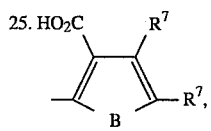

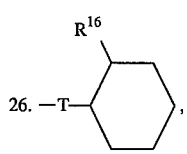

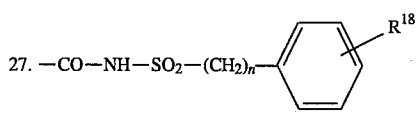

or
28. the radical defined under h) 2., substituted as defined above (see p) 42.) or
29. $R^{15}$ together with $R^{14}$ is —CO—NH—SO$_2$—,
30. —SO$_2$—NH—COO—$R^6$—,
31. —SO$_2$—NH—SO$_2$—NR$^6 R^9$ or
32. —SO$_2$—NH—SO$_2$—$R^6$;

i) $R^{18}$ is hydrogen, methyl or ethyl;
j) T is a single bond, —O—, —CO—, —NHCO— or —OCH$_2$—; and
k) q=0 and L=methylene,
and the other radicals and variables are as defined above.

Compounds which are moreover preferred are azole derivatives of the general formula (I) in which Z is a nitrogen atom, Y and X independently of one another are CR$^2$ and the other symbols are as defined above.

Compounds which are particularly suitable are furthermore azole derivatives of the general formula (I) in which the symbols have the following meaning:

Z is nitrogen,
X and Y independently of one another are CR$^2$,
$R^1$ is $(C_1-C_7)$-alkyl, $(C_3-C_7)$-alkenyl or $(C_3-C_7)$-alkynyl, preferably $(C_3-C_4)$-alkyl,
$R^2$ is hydrogen, halogen, nitro, $(C_1-C_3)$-perfluoroalkyl, cyano, $(C_1-C_{10})$-alkyl, $(C_3-C_{10})$-alkenyl, —CH$_2$OR$^5$, —S(O)$_r$—R$^{19}$, —CO—R$^8$ or —O—R$^6$,
$R^5$ is hydrogen or $(C_1-C_6)$-alkyl,
$R^6$ and $R^9$ are
1. hydrogen,
2. $(C_1-C_6)$-alkyl, which can be substituted by 1 to 3 radicals from the series comprising (C₁–C₆)-alkoxy, which can be substituted in turn by 1 to 3 radicals from the series comprising hydroxyl, (C₁–C₆)-alkoxy, amino, mono-(C₁–C₆)-alkylamino and di-(C₁–C₆)-alkylamino, (C₂–C₁₀)-alkenyl, hydroxyl, amino, mono-(C₁–C₆)-alkylamino, di-(C₁–C₆)-alkylamino, (C₁–C₆)-alkoxycarbonylamino, (C₆–C₁₀)-aryl, (C₆–C₁₀)-aryl-(C₁–C₃)-alkyl, (C₁–C₉)-heteroaryl, carboxyl and (C₁–C₄)-alkoxycarbonyl;

3. (C₃–C₈)-cycloalkyl,
4. (C₃–C₆)-cycloalkyl-(C₁–C₄)-alkyl,
5. (C₆–C₁₂)-aryl, preferably phenyl,
6. (C₆–C₁₀)-aryl-(C₁–C₄)-alkyl,
7. (C₁–C₉)-heteroaryl, which can be partly or completely hydrogenated,
8. (C₁–C₉)-heteroaryl-(C₁–C₃)-alkyl, in which the heteroaryl part can be partly or completely hydrogenated,
9. a radical as defined above under 5., 6., 7. and 8., substituted by 1 or 2 identical or different radicals from the series comprising halogen, hydroxyl, (C₁–C₄)-alkyl, methoxy, nitro, cyano, CO₂R³, trifluoromethyl, —NR¹¹R¹² and

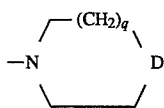

10. (C₁–C₆)-alkyl, in which 1 to all the H atoms are replaced by fluorine,
11. (C₂–C₆)-alkenyl or (C₃–C₆)-alkenoyl,
12. (C₃–C₈)-cycloalkenyl,
13. (C₃–C₈)-cycloalkenyl-(C₁–C₃)-alkyl,
14. (C₆–C₁₀)-aryl-(C₁–C₄)-alkyl,
15. (C₆–C₁₀)-aryl-(C₃–C₆)-alkenyl,
16. (C₁–C₉)-hetaryl-(C₃–C₆)-alkenyl,
17. (C₃–C₆)-alkynyl,
18. (C₆–C₁₀)-aryl-(C₃–C₆)-alkynyl,
19. (C₁–C₉)-hetaryl-(C₃–C₆)-alkynyl, or
20. R⁶ and R⁹, together with the N atom carrying them, are a hetaryl, which can also be partly or completely hydrogenated, R⁷ is hydrogen,
R⁸ is hydrogen or —OR⁶,
R¹¹ and R¹² independently of one another are hydrogen or (C₁–C₄)-alkyl,
D is —NR¹³, —O or —CH₂,
R¹³ is hydrogen or (C₁–C₄)-alkyl,
A is a biphenyl radical, which is substituted by a radical R¹⁵ or by R¹⁴ and R¹⁵ together,
R¹⁵ is —SO₂—NR⁷—CO—NR⁶R⁹, —SO₂—NH—COO—R⁶, —SO₂—NH—SO₂—NR⁶—R⁹, —SO₂—NH—CO—R⁶ or —SO₂—NH—SO₂—R⁶; or
R¹⁴ and R¹⁵ together can be —CO—NH—SO₂—,
L is —CH₂—,
q is zero and
r is zero, 1 or 2,
and physiologically tolerated salts thereof.

Compounds of the formula (I) and physiologically tolerated salts thereof can be prepared by alkylating compounds of the formula (IIa)

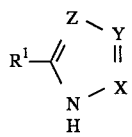 (IIa)

in which R¹, X, Y and Z are as defined above, with compounds of the formula (IIIa)

U—L—(O)_q—A       (IIIa)

in which L, A and q are as defined above and U is a leaving group, splitting off again any protective groups temporarily introduced, if appropriate converting the resulting sulfonamides of the formula (I) into urethanes of the formula (I), converting resulting sulfonamides of the formula (I) or resulting urethanes of the formula (I), and if appropriate converting the resulting compounds of the formula (I) into their physiologically tolerated salts.

Suitable leaving groups U are preferably nucleofugic groups (cf. Angew. Chem. 72 [1960] 71), such as halogen, o-toluenesulfonate, mesylate or triflate.

Processes for the preparation of the precursors of the formulae (IIa) and (IIIa) are known, inter alia, from U.S. Pat. No. 4,355,044, EP-A-324 377 and EP-A-323 841.

Other processes are described by G. L'abbe (Chem. Rev. 69, 345 [1969]), T. Srodsky ("The Chemistry of the Azido Group", Wiley, New York, 1971, page 331), H. Wamhoff ("Comprehensive Heterocyclic Chemistry") and by S. Katritzky Ed., Pergamon Press, New York [1984]). Another process for the preparation of compounds of the formula (IIa) starts from 1-cyanoglyoxylic acid 2-oxime derivatives and, after reduction of the oxime by reducing agents which are known from the literature and addition of mercapto compounds onto the nitrile group using suitable protective groups, gives precursors which can be cyclized to imidazoles under dehydrating conditions. Mixtures of PCl₅ and dimethylaminopyridine (DMAP), POCl₃ and SOCl₂ and mixtures thereof with DMAP, inter alia, can be used for the cyclization step.

The oxidation of the thio compounds of the formula (I) where R² is —S(O)ᵣR¹⁹, in which r is zero or 1, to give the corresponding sulfones and sulfoxides is preferably carried out using peracids in suitable solvents, such as, for example, methylene chloride.

Corresponding benzyl halides, rosylares, mesylates or triflates or corresponding alkyl halides, tosylates, mesylates or triflates, for example, are suitable for alkylation of the azoles of the formula (IIa).

The alkylation is carried out in an analogous manner to processes which are known in principle.

Azole derivatives of the formula (IIa) are metallized, for example, in the presence of a base. Preferred bases are metal hydrides of the formula MH, such as, for example, lithium hydride, sodium hydride or potassium hydride, in, for example, dimethylformamide or dimethyl sulfoxide as a solvent, or metal alkoxides of the formula MOR, in which R is methyl, ethyl or t-butyl, and the reaction is carried out in the corresponding alcohol, dimethylformamide or dimethyl sulfoxide. The azole salts thus formed are dissolved in an aprotic solvent, such as dimethylformamide or dimethyl sulfoxide, and a suitable amount of alkylating reagent is added.

An alternative possibility for the deprotonation of the azole derivatives is, for example, reaction with potassium carbonate in dimethylformamide or dimethyl sulfoxide.

The reactions are carried out at temperatures below room temperature up to the boiling point of the reaction mixture, preferably between +20° C. and the boiling point of the reaction mixture, for about 1 to 10 hours.

The biphenyl derivatives can be synthesized, for example, from arylboronic acid derivatives by coupling with substituted aryl halides using transition metal catalysts, in particular palladium. Corresponding reactions are described by R. B. Miller et al. (Organo-metallics 1984, 3, 1261) or by A. Zuzuki et al. (Synthetic Commun. 11 (7), 513 [1981]).

The sulfonylurethanes of the formula (I) can be obtained from corresponding sulfonamides of the formula (I) by reaction with chlorocarbonic acid esters in inert high-boiling solvents, such as, for example, toluene, at temperatures of about 100° C. or the boiling points of the corresponding solvents.

Sulfonyl-sulfonamides can be prepared analogously from the corresponding sulfonamides by reaction with sulfonic acid chlorides or sulfamoyl chlorides.

If necessary, the sulfonamide radical can be produced starting from an amino group, by means of a Meerwein reaction. For this, the hydrochloride of the amine is first diazotized and the diazotization product is then reacted with sulfur dioxide in glacial acetic acid in the presence of a copper catalyst. Subsequent action of ammonia leads to the sulfonamido group.

Alternatively, a corresponding thiophenol can be converted into a sulfonamide by oxidation with chlorine and subsequent action of ammonia.

Compounds which are additionally preferably employed for the treatment of disturbances in cardiac rhythm are the compounds of the formula (III), in which the symbols have the following meaning:

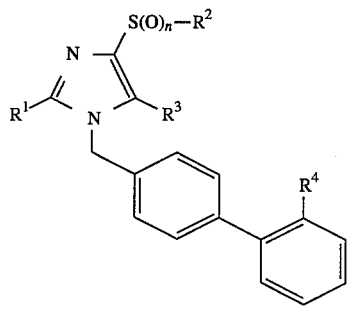

a) $R^1$ is $(C_1-C_7)$-alkyl, $(C_3-C_7)$-alkenyl or $(C_3-C_7)$-alkynyl; in particular $(C_1-C_3)$-alkyl, preferably n-propyl or ethyl, but in particular n-propyl b) $R^2$ is $(C_1-C_6)$-alkyl, preferably methyl c) $R^3$ is $-CO-R^6$ d) $R^4$ is
  $SO_2-NH-CO-NR^7R^9$,
  $SO_2-NH-COO-R^7$,
  $SO_2-NH-CO-R^7$ or
  $SO_2N=CH-N(CH_3)_2$ e) $R^6$ is hydrogen or $OR^7$ f) $R^7$ and $R^9$ are identical or different and are hydrogen, $(C_1-C_6)$-alkyl, preferably methyl, ethyl or propyl, $(C_3-C_8)$-cycloalkyl, $(C_3-C_6)$-cycloalkyl-$(C_1-C_3)$-alkyl, $(C_6-C_{12})$-aryl, preferably phenyl or $(C_6-C_{10})$-aryl-$(C_1-C_4)$-alkyl, $(C_2-C_6)$-alkenyl, $(C_3-C_6)$-alkenoyl or $(C_3-C_6)$-alkynyl g) n is 0, 1 or 2, preferably 0, and tolerated salts thereof.

The invention furthermore relates to the use of compounds of the formula (II)

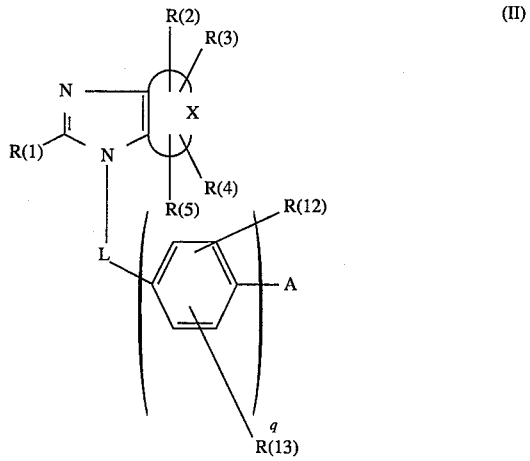

in which the symbols have the following meaning:

X is a monocyclic radical having 3, 4 or 5 ring atoms or a bicyclic radical having 8–10 ring atoms, which can be completely or partly hydrogenated and in which one or more CH or $CH_2$ groups can be replaced by N, NH or O;

R(1) is
1. $(C_1-C_{10})$-alkyl,
2. $(C_3-C_{10})$-alkenyl,
3. $(C_3-C_{10})$-alkynyl,
4. OR(6),
5. $(C_3-C_8)$-cycloalkyl,
6. $(C_4-C_{10})$-cycloalkylalkyl,
7. $(C_5-C_{10})$-cycloalkylalkenyl,
8. $(C_5-C_{10})$-cycloalkynyl,
9. $(CH_2)_m-B-(CH_2)_n-R(7)$,
10. benzyl,
11. a radical as defined under 1., 2., 3. or 9., which is monosubstituted by $CO_2R(6)$,
12. a radical as defined under 1., 2., 3. or 9. in which 1 to all the H atoms are replaced by fluorine or
13. the radical defined under 10., which is substituted on the phenyl by 1 or 2 identical or different radicals from the series comprising halogen, $(C_1-C_4)$-alkoxy and nitro;

R(2), R(3), R(4) and R(5) are identical or different and are
1. Hydrogen, halogen, hydroxyl, cyano, nitro, sulfo, formyl, benzoyl, $(C_1-C_6)$-acyl, $(C_1-C_8)$-acryloxy, mercapto, carboxyl, $(C_1-C_4)$-alkoxycarbonyl,
2. a linear or branched, optionally substituted alkyl, alkenyl, alkoxy or alkylthio radical containing up to 6 carbon atoms,
3. an aryl, arylalkyl or arylalkenyl radical, in which the alkyl and alkenyl substituent is unbranched or branched and contains up to 6 carbon atoms and the aryl substituent is a monocyclic radical having 5 or 6 ring atoms or fused rings having 8 to 14 ring atoms, which contain one or more hetero atoms, such as O, N or S, and are optionally substituted, or
4. a radical

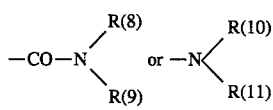

R(6) is
1. hydrogen,
2. $(C_1-C_8)$-alkyl,
3. $(C_3-C_8)$-cycloalkyl,
4. phenyl,
5. benzyl or
6. the radical defined under 2. in which 1 to all the H atoms are replaced by fluorine;

R(7) is
1. hydrogen,
2. $(C_1-C_6)$-alkyl,
3. $(C_3-C_8)$-cycloalkyl,
4. $(C_2-C_4)$-alkenyl or
5. $(C_2-C_4)$-alkynyl, R(8) and R(9) or R(10) and R(11) either are identical or different and are
1. hydrogen,
2. $(C_1-C_6)$-alkyl or $(C_1-C_6)$-alkenyl, unsubstituted or substituted by halogen, hydroxyl or $(C_1-C_6)$-alkoxy or
3. aryl or $(C_1-C_6)$-alkylaryl, in which the aryl radical is monocyclic with 5 or 6 ring atoms or bicyclic with 8–10 ring atoms, optionally contains one or more hetero atoms, such as O, N and S, and is substituted by 1 or 2 identical or different radicals from the series comprising halogen, hydroxyl, nitro, $(C_1-C_6)$-alkyl, $(C_1-C_6)$-alkenyl, $(C_1-C_4)$-alkanoyl, $(C_1-C_4)$-alkanoyloxy and $CO_2R(6)$;

or
R(8) and R(9) and R(11), together with the N atom carrying them, form a 4- to 8-membered ring, which is saturated or unsaturated, can contain a further hetero atom chosen from the group comprising N, O and S and is unsubstituted or substituted by halogen, hydroxyl, $(C_1-C_4)$-alkyl, $(C_1-C_4)$-alkenyl, $(C_1-C_4)$-alkyloxy and $CO_2R(6)$, or
R(10) and R(11) are either identical or different and are an acyl radical having up to 6 carbon atoms or a $(C_1-C_6)$-alkyl or $(C_6-C_{12})$-aryl radical, which are optionally substituted by halogen or $(C_1-C_6)$-alkyl radicals;

L is $(C_1-C_3)$-alkanediyl;

R(12) and R(13) are identical or different and are
1. hydrogen,
2. halogen,
3. nitro,
4. $(C_1-C_4)$-alkyl or
5. $(C_1-C_2)$-alkoxy;

q is zero or 1;

A is either
1. the radical of a heterocyclic compound having 5–10 ring atoms, which can be mono- or bicyclic, and of which up to 9 ring atoms are carbon atoms, and which is unsubstituted or substituted by up to 6, preferably up to 3, identical or different radicals R(14) and R(15), or
2. a biphenyl radical, which is unsubstituted or substituted by up to 4, preferably up to 2, identical or different radicals R(14) and R(15), but A is necessarily substituted by at least one radical defined under R(15) 18., 19., 28., 40. or 42 and q is zero;

R(14) is
1. halogen,
2. oxo,
3. nitroso,
4. nitro,
5. amino,
6. cyano,
7. hydroxyl,
8. $(C_1-C_6)$-alkyl,
9. $(C_1-C_4)$-alkanoyl,
10. $(C_1-C_4)$-alkanoyloxy,
11. $CO_2R(6)$,
12. methanesulfonylamino,
13. trifluoromethanesulfonylamino,
14. —CO—NH—OR(16),
15. —$SO_2$—NR(17)R(18),
16. —$CH_2$—OR(18),
17. $(C_1-C_4)$-heteroaryl-$(CH_2)_q$—, preferably 1-tetrazolyl,
18. $(C_7-C_{13})$-aroyl,

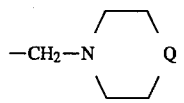 19.

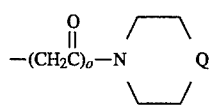 20.

$(C_6-C_{12})$-aryl; 21.

or
21. $(C_6-C_{12})$-aryl;

R(15) is
1. hydrogen,
2. $(C_1-C_6)$-alkyl,
3. $(C_3-C_8)$-cycloalkyl,
4. $(C_6-C_{12})$-aryl,
5. $(C_7-C_{13})$-aroyl,
6. $(C_1-C_4)$-alkoxy,
7. $(C_1-C_4)$-alkanoyloxy,
8. $(C_1-C_9)$-heteroaryl,
9. $CO_2R(6)$,
10. halogen,
11. cyano,
12. nitro,
13. NR(17)R(18),
14. hydroxyl,
15. —CO—NH—CHR(19)—$CO_2R(6)$,
16. sulfo,
17. —$SO_3R(6)$,
18. —$SO_2$—NR(18)—CO—NR(17)R(16), —$SO_2$—NR(18)—CO—OR(17), —$SO_2N(CO$—O—$R(17))_2$ or —$SO_2$—NR(18)—CS—NR(17)R(16),
19. —NR(18)—SO—NR(17)—$SO_2$—$CH_2$—R(18),
20. —$C(CF_3)_2OH$,
21. phosphonooxy,
22. —$PO_3H_2$, 23. —NH—PO(OH)$_2$,
24. —S(O)$_r$R(17),
25. —CO—R(20),
26. —CO—NR(17)R(16), 27. 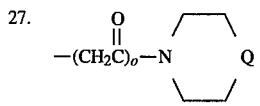

28. 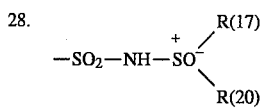

29. 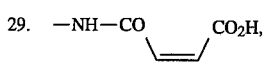

30. 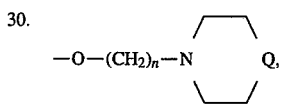

31. 5-tetrazolyl-NH—CO—,

32. —CO—NH—NH—SO$_2$CF$_3$,

33. 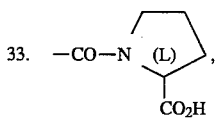

34. 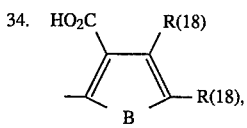

35. 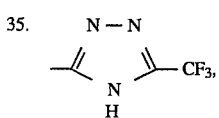

36. 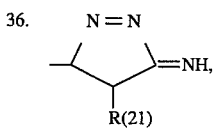

37. 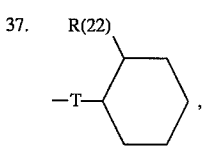

38. 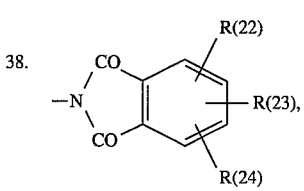

39. —CO—NH—SO$_2$—R(6),
40. —SO$_2$—NH—CO—R(17),
41. the radical defined under 4., substituted by one or two identical or different radicals from the series comprising halogen, cyano, nitro, NR(17)R(18) and hydroxyl, or
42. R(15), together with R(14), is —CO—NH—SO$_2$—;

R(16) and R(17) are identical or different and are
1. hydrogen,
2. (C$_1$–C$_6$)-alkyl,
3. (C$_3$–C$_8$)-cycloalkyl,
4. (C$_6$–C$_{12}$)-aryl, preferably phenyl,
5. (C$_6$–C$_{10}$)-aryl-(C$_1$–C$_4$)-alkyl,
6. (C$_1$–C$_9$)-heteroaryl, which can be partly or completely hydrogenated, preferably 2-pyrimidinyl, 1-piperidinyl or quinuclidinyl,
7. (C$_3$–C$_6$)-alkenoyl,
8. a radical as defined under 4., 5., 6., 9., 14., 15., 16., 18., 19., or 20., substituted by 1 or 2 identical or different radicals from the series comprising hydroxyl, methoxy, nitro, cyano, CO$_2$R(6), trifluoromethyl, —NR(25)R(26) and

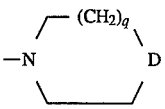

9. (C$_1$–C$_9$)-heteroaryl-(C$_1$–C$_3$)-alkyl, in which the heteroaryl part can be partly or completely hydrogenated,
10. the radical defined under 2. in which 1 to all the H atoms are replaced by fluorine,
11. (C$_2$–C$_6$)-alkenyl,
12. (C$_3$–C$_8$)-cycloalkenyl,
13. (C$_3$–C$_8$)-cycloalkenyl-(C$_1$–C$_3$)-alkyl,
14. (C$_3$–C$_8$)-cycloalkyl-(C$_1$–C$_4$)-alkyl,
15. (C$_6$–C$_{10}$)-aryl-(C$_3$–C$_6$)-alkenyl,
16. (C$_1$–C$_9$)-hetaryl-(C$_3$–C$_6$)-alkenyl,
17. (C$_3$–C$_6$)-alkynyl,
18. (C$_6$–C$_{10}$)-aryl-(C$_3$–C$_6$)-alkynyl,
19. (C$_1$–C$_9$)-hetaryl-(C$_3$–C$_6$)-alkynyl,
20. a radical of the formula

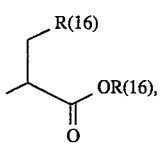

in which R(16) cannot have the meaning of 20., or
21. R(16) and R(17), together with the N atom carrying them, form a hetaryl, which can also be partly or completely hydrogenated;
R(18) is
1. hydrogen,
2. (C$_1$–C$_6$)-alkyl,
3. (C$_3$–C$_8$)-cycloalkyl,
4. (C$_6$–C$_{12}$)-aryl-(C$_1$–C$_6$)-alkyl, preferably benzyl,
5. phenyl or
6. (C$_1$–C$_9$)-heteroaryl;
R(19) is
1. hydrogen,
2. (C$_1$–C$_6$)-alkyl,
3. (C$_3$–C$_8$)-cycloalkyl,
4. phenyl or
5. benzyl R(20) is
1. hydrogen,
2. $(C_1-C_6)$-alkyl,
3. $(C_3-C_8)$-cycloalkyl,
4. phenyl-$(CH_2)_q$—,
5. OR(19),
6. NR(25)R(26) or 7. 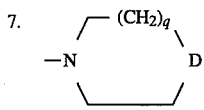

R(21) is cyano, nitro or $CO_2R(18)$;
R(22) is $CO_2R(6)$ or $CH_2CO_2R(6)$;
R(23) is hydrogen, halogen, $(C_1-C_4)$-alkyl or $(C_1-C_4)$-alkoxy;
R(24) is hydrogen, $(C_1-C_4)$-alkyl or phenyl;

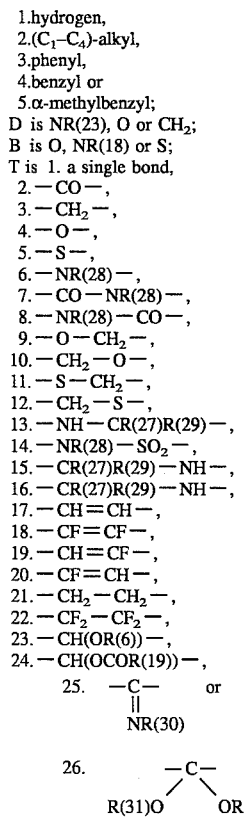

1. hydrogen,
2. $(C_1-C_4)$-alkyl,
3. phenyl,
4. benzyl or
5. α-methylbenzyl;
D is NR(23), O or $CH_2$;
B is O, NR(18) or S;
T is 1. a single bond,
2. —CO—,
3. —$CH_2$—,
4. —O—,
5. —S—,
6. —NR(28)—,
7. —CO—NR(28)—,
8. —NR(28)—CO—,
9. —O—$CH_2$—,
10. —$CH_2$—O—,
11. —S—$CH_2$—,
12. —$CH_2$—S—,
13. —NH—CR(27)R(29)—,
14. —NR(28)—$SO_2$—,
15. —CR(27)R(29)—NH—,
16. —CR(27)R(29)—NH—,
17. —CH=CH—,
18. —CF=CF—,
19. —CH=CF—,
20. —CF=CH—,
21. —$CH_2$—$CH_2$—,
22. —$CF_2$—$CF_2$—,
23. —CH(OR(6))—,
24. —CH(OCOR(19))—,
25. —C— or
       ‖
       NR(30)
26.   —C—
     /   \
   R(31)O   OR(32);

R(27) and R(29) are identical or different and are hydrogen, $(C_1-C_5)$-alkyl, phenyl, allyl or benzyl;
R(28) is hydrogen, $(C_1-C_6)$-alkyl, benzyl or allyl;
R(30) is
1. NR(27)R(28),
2. ureido,
3. thioureido,
4. toluene-4-sulfonyl or
5. benzenesulfonylamino;
R(31) and R(32) are identical or different and are $(C_1-C_4)$-alkyl, or together are —$(CH_2)_q$—;
Q is $CH_2$, NH, O or S;
n is an integer from 1 to 5;
m is an integer from 0 to 3;
o is an integer from 1 to 10; and
r is zero, 1 or 2,
and physiologically tolerated salts thereof.

Alkyl, alkenyl and alkynyl can be straight-chain or branched. The same applies to radicals derived therefrom, such as alkanoyl or alkoxy.

Cycloalkyl is also understood as meaning alkyl-substituted rings.

$(C_6-C_{12})$-Aryl is, for example, phenyl, naphthyl or biphenylyl, preferably phenyl. The same applies to radicals derived therefrom, such as aroyl or aralkyl.

$(C_1-C_9)$-Heteroaryl is understood as meaning, in particular, radicals which are derived from phenyl or naphthyl, in which one or more CH groups are replaced by N and/or in which at least two adjacent CH groups are replaced by S, NH or O (to form a five-membered aromatic ring). Furthermore, 1 or both atoms of the condensation site of bicyclic radicals (such as in indolizinyl) can also be an N atom.

These are, for example, furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyradiazinyl, indolyl, indazolyl, quinolyl, isoquinolyl, phthalazinyl, quinoxalinyl, quinazolinyl and quinolinyl.

The fused heterobicyclic compound AH from which the radical A is derived is understood as meaning, in particular, a bicyclic ring system having 8 to 10 ring atoms, up to 9 ring atoms of which are carbon atoms, and in which two adjacent atoms are common constituents of the two rings. One or both of these rings are derived formally from benzene, in which one or more CH groups are replaced by N, $O^+$ and $S^+$ and/or in which two adjacent CH groups are replaced by S, NH or O (to form a five-membered aromatic ring).

A is, for example, a radical of benzothiophene, benzofuran, indole, isoindole, indazole, benzimidazole, quinoline, isoquinoline, phthalazine, quinoxaline, quinazoline, cinnoline, benzothiazole, benzothiazole 1,1-dioxide, coumarin, chroman, benzoxazole, benzisothiazole, benzodiazine, benzotriazole, benzotriazine, benzoxazine, imidazopyridine, imidazo-pyrimidine, imidazo-pyrazine, imidazo-pyridazine, imidazo-thiazole, pyrazolopyridine, thienopyridine and pyrrolopyrimidine. The heterobicyclic compound AH mentioned can also be partly or completely hydrogenated. Preferably, however, one ring of AH remains aromatic, a benzo-fused heterobicyclic compound AH being particularly preferred.

In the case of S-containing and/or partly saturated radicals, the bicyclic radical can also be oxo-substituted, for example, as is the case in the radical of benzo-1,2,3-triazinone.

A is linked to the group

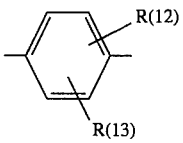

from the isocyclic or from the heterocyclic part via an alkanediyl bridge L if q is zero and via a single bond if q is 1.

An iso- or heterocyclic compound $XH_2$ from which the mono- or bicyclic radical X is derived is understood as meaning, for example, a radical of cyclopentane, cyclohexane, cycloheptane, cyclopentene, cyclohexene, cycloheptene, benzene, naphthalene, furan, thiophene, pyrrole, pyridine, pyridazine, pyrimidine, piperidine, piperazine, morpholine, indole, indazole, oxazole, isoaxazole, quinoline, isoquinoline, benzothiophene, benzofuran, benzothiazole, benzoxazole, imidazopyridine, imidazopyrimidine and rufopyridine. Halogen is fluorine, chlorine, bromine and iodine.

Physiologically tolerated salts of compounds of the formula (II) are understood as meaning both organic and inorganic salts thereof, such as are described in Remington's Pharmaceutical Sciences, 17th Edition, page 1418 (1985). Because of their physical and chemical stability and solubility, the sodium, potassium, calcium and ammonium salts, inter alia, are preferred for acid groups, and salts with hydrochloric acid, sulfuric acid, phosphoric acid, carboxylic acids or sulfonic acids, such as acetic acid, citric acid, benzoic acid, maleic acid, fumaric acid, tartaric acid and p-toluenesulfonic acid, inter alia, are preferred for basic groups.

Compounds which are preferably employed against disturbances in cardiac rhythm are those of the formula (IV)

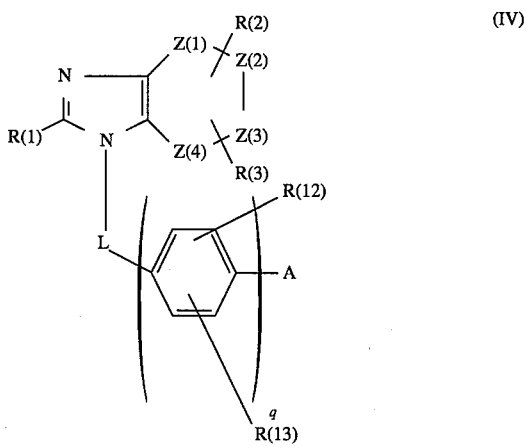

in which the symbols have the following meaning:
Z(1), Z(2), Z(3) and Z(4) are
1. —CH—,
2. —CH= or
3. a radical defined under 2. in which 1 or 2 methine groups are replaced by nitrogen; preferably, Z(4) is N, R(1) is
1. $(C_1-C_{10})$-alkyl,
2. $(C_3-C_{10})$-alkenyl,
3. $(C_3-C_{10})$-alkynyl,
4. $(C_3-C_8)$-cycloalkyl,
5. benzyl or
6. benzyl which is substituted as described above;

R(2) and R(3) are identical or different and are
1. hydrogen,
2. hydroxyl,
3. halogen,
4. a linear or branched $(C_1-C_6)$-alkyl radical, unsubstituted or substituted by one or more identical or different substituents from the series comprising halogen, hydroxyl, $(C_1-C_4)$-alkoxy, $(C_1-C_4)$-alkylthio and mercapto or
5. —$CO_2R(6)$;

T is a single bond, —O—, —CO—, —NHCO— or —$OCH_2$—, and the other radicals and variables are as defined above.

Particularly preferred compounds of the formula (IV) are those in which
R(1) is $(C_1-C_7)$-alkyl, $(C_3-C_7)$-alkenyl or $(C_3-C_7)$-alkynyl;
R(6) is hydrogen or $(C_1-C_4)$-alkyl;
R(12) and R(13) are identical or different and are hydrogen or $(C_1-C_4)$-alkyl;

(R14) is
1. $(C_1-C_4)$-alkyl,
2. $(C_1-C_4)$-alkoxy,
3. cyano,
4. amino,
5. nitro,
6. fluorine, chlorine or bromine,
7. $(C_1-C_4)$-heteroaryl-$CH_2$,
8. $(C_1-C_4)$-alkanoyloxy,
9. $(C_1-C_4)$-alkanoyl,
10. benzoyl or
11. tetrazolyl;

R(15) is
1. $(C_1-C_4)$-alkyl,
2. $(C_6-C_{12})$-aryl,
3. $(C_1-C_3)$-alkanoyloxy,
4. $(C_1-C_4)$-alkoxy,
5. $(C_1-C_9)$-heteroaryl, preferably 5-tetrazolyl,
6. cyano,
7. nitro,
8. hydroxyl,
9. $SO_3R(6)$,
10. chlorine, bromine,
11. $CO_2R(6)$,
12. CO—NH—R(19),
13. CO—R(20),
14. $SO_2$—NR(18)—CO—NR(17)R(16),
15. $SO_2$—NR(18)—CO—O—R(17) or $SO_2N(CO—OR(17))_2$,
16. CO—CHR(19)—$CO_2H$,
17. $(C_1-C_4)$-alkyl—$CO_2H$,
18. NH—CO—NH—$SO_2$—$CH_2$—R(19), 20. 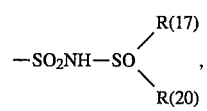

21. 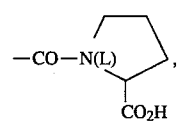

22. 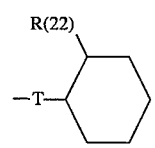

or
23. (R14), together with R(15), is —CO—NH—$SO_2$;
L is —$CH_2$—;
R(18) is hydrogen; and
R(25) and R(26) independently of one another are hydrogen or $(C_1-C_4)$-alkyl,
and physiologically tolerated salts thereof.

The process for the preparation of compounds of the formula (II) comprises alkylating compounds of the formula (IIIb)

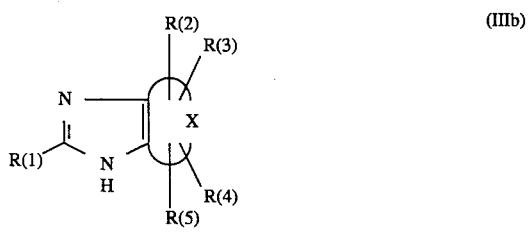

in which R(1), R(2), R(3), R(4), R(5) and X are as defined above, with compounds of the formula (IVb)

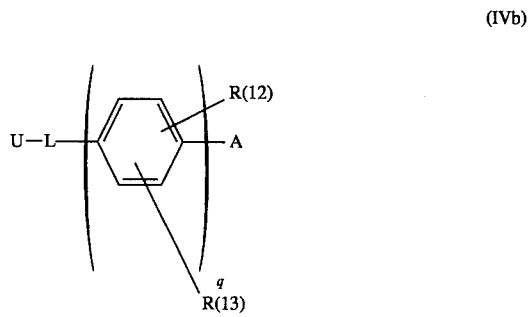

in which L, q, R(12), R(13) and A are as defined above and U is a leaving group, splitting off again any protective groups temporarily introduced, and if appropriate converting the resulting compounds of the formula (II) into their physiologically tolerated salts.

Suitable leaving groups U are preferably nucleofugic groups (cf. Angew. Chem. 72 (1960)), such as halogen, o-toluenesulfonate, mesylate or triflate.

Processes for the preparation of the precursors of the formula (IIIb) are known, inter alia, from U.S. Pat. No. 4,880,804, DE 3 911 603, EP-A-399 731, EP-A-399 732, EP-A-400 835, EP-A-400 974, EP-A-415 886, EP-A-420 237, EP-A-425 921 and EP-A-434 038.

Corresponding benzyl halides, rosylares, mesylates or triflates or corresponding alkyl halides, tosylates, mesylates or triflates, for example, are suitable for alkylation of the compounds of the formula (IIIb).

These compounds are prepared in a manner which is known per se, for example by halogenation of the corresponding methyl precursors. N-bromosuccinimide is preferably employed for this, cf., for example, J. Org. Chem. 44, 4733 (1979) and Helv. Chim. Acta 62, 2661 (1979).

The benzimidazole, benzothiophene, imidazo-pyridine and imidazo-pyrimidine derivatives having a $CH_3$ group on the nucleus are synthesized, inter alia, by the method of R. P. Dickson et al. in J. Med. Chem. 29, 1937 (1986), E. Abignente et el. in J. Heterocyclic Chem. 26, 1875 (1989), A. Koubsack et el. in J. Org. Chem. 41, 3399 (1976) and by the method of F. Santer et al. in Mh. Chem. 99, 715 (1968).

The biphenyl derivatives can be synthesized, for example, starting from arylboronic acid derivatives by coupling with substituted aryl halides using transition metal catalysts, in particular palladium. Corresponding reactions are described by R. B. Miller et al. (Organometallics 1984, 3, 1261) or by A. Zuzuki et al. (Synthetic Commun. 11 (7), 513 (1981)).

The sulfonylurethane derivatives of the formula (II) can be obtained from corresponding sulfonamides of the formula (II) by reaction with chlorocarbonic acid esters or by reaction with dimethyl dicarbonate and bases, such as, for example, potassium carbonate, in inert solvents at temperatures up to the boiling point of the corresponding solvent.

The sulfonylurea derivatives of the formula (II) can be prepared either from the corresponding sulfonamides of the formula (II) by reaction with isocyanates or with 2,2,2-trichloroacetamide derivatives of a suitable amine in inert high-boiling solvents, such as, for example, dimethyl sulfoxide, or from sulfonylurethanes of the formula (II) by the action of the corresponding amine in an inert high-boiling solvent, such as, for example, toluene, at temperatures up to the boiling point of the particular solvent.

If necessary, the sulfonamide radical can be produced starting from an amino group by means of a Meerwein rearrangement. For this, the hydrochloride of the amine is first diazotized and the diazotization product is then reacted with sulfur dioxide in glacial acetic acid in the presence of a copper catalyst. The subsequent action of ammonia leads to the sulfonamide group. The alkylation is carried out in a manner analogous to processes which are known in principle.

The imidazo-fused derivatives of the formula (IIIb) are metallized, for example in the presence of a base. Preferred bases are metal hydrides of the formula MH, such as lithium hydride, sodium hydride or potassium hydride, in, for example, dimethylformamide or dimethyl sulfoxide as the solvent, or metal alkoxides of the formula MOR, in which R is methyl, ethyl or t-butyl, the reaction being carried out in the corresponding alcohol, dimethylformamide or dimethyl sulfoxide. The salts thus formed of the imidazo derivatives are dissolved in an aprotic solvent, such as dimethylformamide or dimethyl sulfoxide, and a suitable amount of alkylating reagent is added.

An alternative possibility for deprotonation of the imdazole derivatives is, for example, reaction with potassium carbonate in dimethylformamide or dimethyl sulfoxide.

The reactions are carried out at temperatures below room temperature up to the boiling point of the reaction mixture, preferably between +20° C. and the boiling point of the reaction mixture, for a period of about 1 to 10 hours.

Of the compounds of the general formulae (I), (II), (III) and (IV), those compounds which contain, as substituents of the biphenyl system, a sulfonylurea grouping, such as, for example, $—SO_2—NR^7—CO—NR^6R^9$, have proven to be particularly advantageous in respect of their metabolism, in particular in humans.

The following compounds are also of particular interest in respect of their therapeutic action on disturbances in cardiac rhythm:

1. ethyl 2-n-butyl-1-[(2'-n-propylaminocarbonylaminosulfonyl-biphenyl- 4-yl)methyl]-4-methylthio-imidazole-5-carboxylate
2. 2-n-butyl-1-[(2'-n-propylaminocarbonylaminosulfonyl-biphenyl- 4-yl)methyl]-4-methylthio-imidazole-5-carboxylic acid
3. ethyl 2-n-propyl-1-[(2'-n-propylaminocarbonylaminosulfonyl-biphenyl- 4-yl)methyl]-4-methylthio-imidazole-5-carboxylate
4. 2-n-propyl-1-[(2'-n-propylaminocarbonylaminosulfonyl-biphenyl- 4-yl)methyl]-4-methylthio-imidazole- 5-carboxylic acid
5. 3-[(2'-allylaminocarbonylaminosulfonyl-biphenyl-4-yl)methyl] -2-ethyl-7-methyl-imidazo[4,5-b]pyridine
6. 5,7-dimethyl-3-[(2'-methoxycarbonylaminosulfonyl-biphenyl- 4-yl)methyl]-2-ethyl-imidazol[4,5-b]pyridine
7. the potassium salt of 2-n-butyl-4-chloro-5-hydroxymethyl- 1-[(2'-(1H-tetrazol-5-yl)-biphenyl-4-yl)methyl] -imidazole, known from EP-A 324 377

8. 5,7-dimethyl-3-[(2'-tetrazoyl-biphenyl-4-yl)methyl]-imidazol[4,5-b]pyridine, known from EP-A 399 731, EP-A 400 974 and N. B. Mantlo, J. Med. Chem. 34, 1991, 2919–2922

9. 2-n-butyl-4-chloro-1-[(2'-(1H-tetrazol-5-yl)-biphenyl-4-yl)-methyl]-imidazol-5-carboxylic acid (cf. P. C. Wong et al., J. Pharmacol. Exp. Ther. 252, 711–718, 1990)

and physiologically tolerated salts thereof, such as the corresponding mono- and dipotassium salts.

Furthermore, treatment of disturbances in cardiac rhythm is also possible using angiotensin II receptor antagonists of the general formulae VI–XX, which are described in the particular prior art stated.

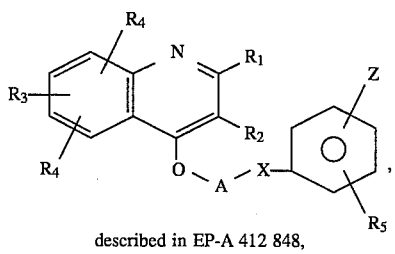

described in EP-A 412 848,

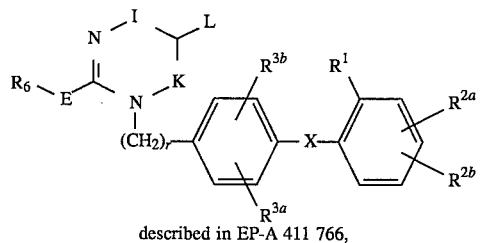

described in EP-A 411 766,

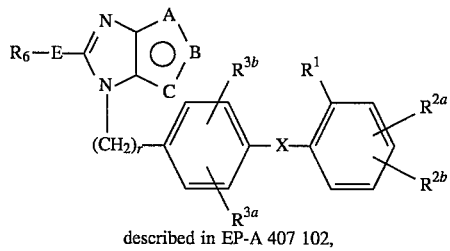

described in EP-A 407 102,

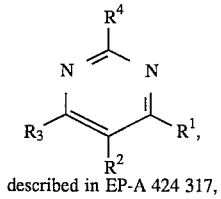

described in EP-A 424 317,

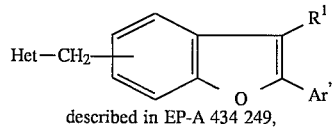

described in EP-A 434 249,

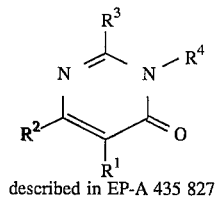

described in EP-A 435 827

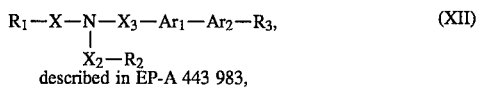

described in EP-A 443 983,

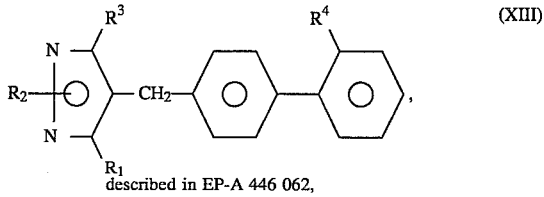

described in EP-A 446 062,

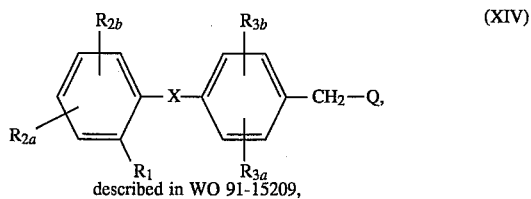

described in WO 91-15209,

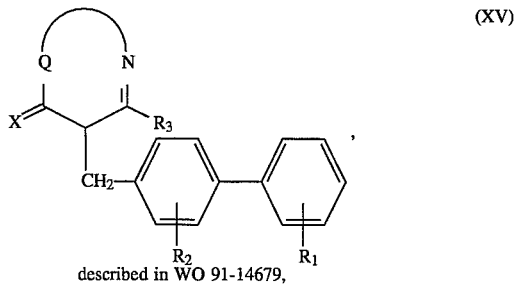

described in WO 91-14679,

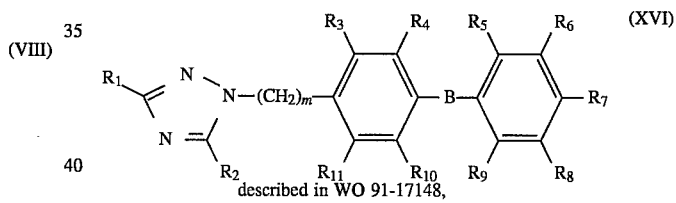

described in WO 91-17148,

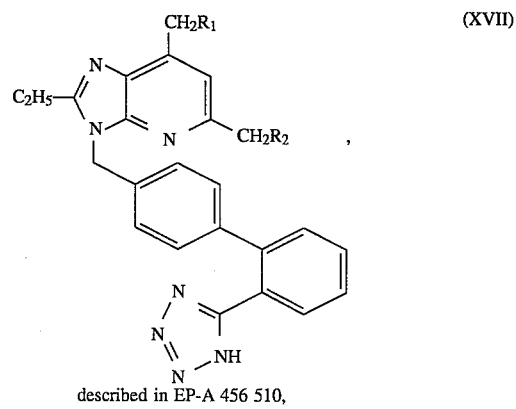

described in EP-A 456 510,

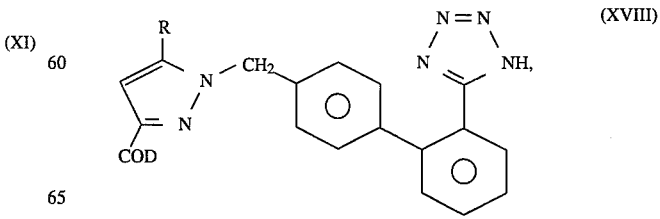

-continued
described in EP-A 411 507,

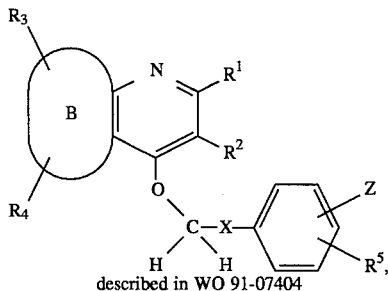

described in WO 91-07404 and

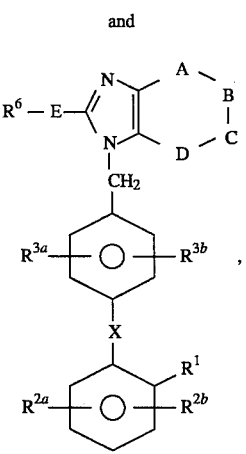

described in EP-A 400 974.

In carrying out the method according to the invention, the angiotensin II receptor antagonists described above can be used on meals, such as monkeys, dogs, cats, rats, humans and the like.

The compounds suitable for the use according to the invention are advantageously incorporated into pharmaceutical preparations in the customary manner. They can be brought into the customary administration forms, such as capsules, tablets, coated tablets, solutions, ointments and emulsions, and also into depot form. If appropriate, the active compound can also be present in microencapsulated form. The preparations can contain physiologically tolerated organic or inorganic auxiliaries or additives, for example granulating substances, adhesives and binders, lubricants, suspending agents, solvents, antibacterial agents, wetting agents and preservatives.

The treatment according to the invention can be effected either via the mucosae or parenterally. Oral and parenteral (such as i.v. or i.m.) use forms are preferred.

For an oral use form, the active compounds are mixed with the additives customary for this purpose, such as excipients, stabilizers or inert diluents, and the mixtures brought into suitable presentation forms, such as tablets, coated tablets, had gelatin capsules, aqueous, alcoholic or oily suspensions or aqueous, alcoholic or oily solutions, by customary methods. Inert excipients which can be used are, for example, gum arabic, magnesium carbonate, potassium phosphate, lactose, glucose or starch, in particular maize starch. The compounds can be formulated as either dry or moist granules. Possible oily excipients or solvents are, for example, vegetable and animal oils, such as sunflower oil or cod-liver oil.

For subcutaneous or intravenous administration, the active compounds, or physiologically tolerated salts thereof, are converted into solution form, into suspensions or emulsions, if desired with the substances customary for this purpose, such as solubilizing agents, an emulsifier or other auxiliaries. Possible solvents for the active combinations and the corresponding physiologically tolerated salts are, for example: water, physiological saline solutions or alcohols, for example ethanol, propanediol or glycerol, and in addition also sugar solutions, such as glucose solutions or mannitol solutions, or also a mixture of the various solvents mentioned.

The compounds described are preferably administered in doses of 0.1 to 100 mg/kg, specifically preferably 0.1 to 50 mg, in particular 1 to 30 mg, being administered once to three times daily.

Investigation of coronary arterial spasms has led to the conclusion that reperfusion-induced ventricular fibrillation is the main cause of sudden cardiac death in humans (V. Elharrer, D. P. Zipes, Am. J. Physiol. 232, H 329 to H 345 (1977)). The majority of victims of sudden death have the characteristic of participation of pernicious ventricular arrhythmias as the last common feature (S. Goldstein et al., J. Am. Coll. Cardiol. 3, 1111 (1984)).

Reperfusion is also to be encountered after recanalization of a previously blocked coronary artery by angioplasty or thrombotic processes during subsidence of acute myocardial ischemias or cardiac infarction (P. Rentrop et al., Circulation 63, 307 (1981)). Reperfusions of the entire heart additionally occur under surgical conditions during cardiopulmonary bypass with ischemic cardiac arrest. During surgical reperfusion, various hazardous arrhythmias, including ventricular fibrillation, are often observed (A. S. Manning, J. Mol. Cell. Cardiol. 16, 497 to 518 (1984)).

The activity of the compounds described above on disturbances in cardiac rhythm is demonstrated by the activity in the model of the isolated, working heart of the rat with postischemic reperfusion arrhythmias.

EXAMPLE 1

The result with 2-n-propyl-1-[(2'-n-propylaminocarbonylaminosulfonyl-biphenyl- 3-yl)-methyl]-4-methylthio-imidazole- 5-carboxylic acid (formula XXI) is described as an example:

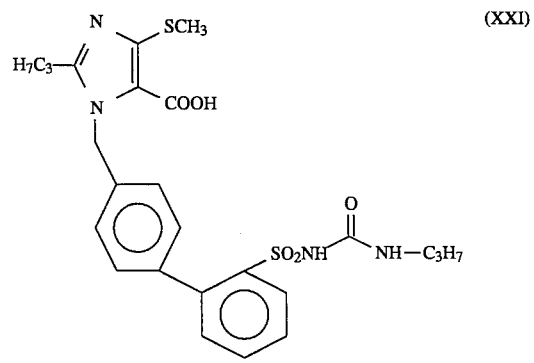

Experiment

Action of the $AT_1$ angiotensin II receptor antagonist 2-n-propyl- 1-[(2'-n-propylaminocarbonylaminosulfonyl-biphenyl- 4-yl)methyl]-4-methylthio-imidazole-5-carboxylic acid (formula XXI) on postischemic reperfusion arrhythmias in the isolated, working rat heart.

Method

The preparation of the isolated, working rat heart used in the experiment is described by W. Linz et al. in J. Cardiovasc. Pharmacol. 8 (Supplement 10), pages 91–99 (1986).

After a preischemic perfusion period of 20 minutes, regional myocardial ischemia is induced by constricting the left coronary artery for 15 minutes (ischemic period). The arterial clamp is then opened again and the changes during reperfusion are recorded for 30 minutes (reperfusion period).

In an in vitro experiment, the hearts are perfused with the compound of the formula (XXI) in a concentration of $1\times10^{-6}$ mol/l. The solution is prepared using Krebs-Henseleit buffer.

The measurement parameters are the cardiodynamic parameters, such as the left ventricular pressure for determination of the incidence and duration of the ventricular fibrillation (CF), left ventricular $dP/dt_{max}$ values, heart beat and coronary flow.

Result of the experiment:

Untreated control hearts fibrillate for 16.3 ±3 minutes during a reperfusion period of 30 minutes. The fibrillation incidence is 8 out of 8 hearts (8/8). The rat hearts which had been perfused with the compound of the formula (XXI) fibrillate for 6.2 ±0.9 minutes with an incidence of 7 out of 8 hearts (7/8).

This significant reduction in the ventricular fibrillation rate and the changed fibrillation incidence in isolated ischemic rat hearts demonstrate the protective action of the compound of the formula (XXI) in respect of post-ischemic reperfusion arrhythmias.

The following examples describe the forms of use for treatment of disturbances in cardiac rhythm by the method according to the invention. The compounds of the general formulae I–IV, and also the compounds VI to XX, can be brought into the corresponding forms of use analogously to the examples.

EXAMPLE 2

Preparation of an agent for oral use in the treatment of disturbances in cardiac rhythm.

1000 tablets, each of which comprises 20 mg of 2-n-propyl- 1-[(2'-n-propylaminocarbonylaminosulfonyl-biphenyl- 4-yl)methyl]-4-methylthio-imidazole-5-carboxylic acid, are prepared using the following auxiliaries.

| | |
|---|---|
| 2-n-Propyl-1-[(2'-n-propylaminocarbonylaminosulfonyl-biphenyl-4-yl)methyl]-4-methylthio-imidazole-5-carboxylic acid | 20.0 g |
| Maize starch | 140.0 g |
| Gelatin | 7.5 g |
| Microcrystalline cellulose | 2.5 g |
| Magnesium stearate | 2.5 g |

The 2-n-propyl-1-[(2'-n-propylaminocarbonylaminosulfonyl-biphenyl- 4 -yl)methyl]-4-methylthio-imidazole-5-carboxylic acid and maize starch are mixed with an aqueous gelatin solution. The mixture is dried and ground to granules. The microcrystalline cellulose and magnesium stearate are mixed with the granules. The resulting granules are pressed to 1000 tablets, each tablet comprising 20 mg of the angiotensin II receptor antagonist. These tablets can be used for the treatment of disturbances in cardiac rhythm.

EXAMPLE 3

Analogously to Example 1, 1000 tablets, each of which contains 3 mg of 2-n-propyl-1-[(2'-n-propylaminocarbonylaminosulfonyl-biphenyl- 4-yl)methyl]-4-methylthio-imidazole- 5-carboxylic acid, are prepared by using 3 g of this compound in the mixture described in Example 2.

EXAMPLE 4

Gelatin capsules, each of which contains 20 mg of 2-n-propyl- 1-[(2'-n-propylaminocarbonylaminosulfonyl-biphenyl- 4-yl)methyl]-4-methylthio-imidazole-5-carboxylic acid, are filled with the following mixture:

| | |
|---|---|
| 2-n-Propyl-1-[(2'-n-propylaminocarbonylaminosulfonyl-biphenyl-4-yl)methyl]-4-methylthio-imidazole-5-carboxylic acid | 20 mg |
| Potassium stearate | 1 mg |
| Lactose | 214 mg |

These capsules can be used for the treatment of disturbances in cardiac rhythm.

EXAMPLE 5

Analogously to Example 4, capsules, each of which contains 3 mg of 2-n-propyl-1-[(2'-n-propylaminocarbonylaminosulfonyl-biphenyl- 4-yl)methyl]-4-methylthio-imidazole- 5-carboxylic acid, are prepared using 3 mg of active compound.

EXAMPLE 6

The preparation of an injection solution for the treatment of disturbances in cardiac rhythm is described below:

| | |
|---|---|
| 2-n-Propyl-1-[(2'-n-propylaminocarbonylaminosulfonyl-biphenyl-4-yl)methyl]-4-methylthio-imidazole-5-carboxylic acid | 1 g |
| Methylparaben | 5 g |
| Propylparaben | 1 g |
| Sodium chloride | 25 g |
| Water for injections | 5 l |

The 2-n-propyl-1-[(2'-n-propylaminocarbonylaminosulfonyl-biphenyl- 4-yl)methyl]-4-methylthio-imidazole-5-carboxylic acid, the preservatives and the sodium chloride are dissolved in 3 l of water for injections and the solution is made up to 5 l with water for injections. The solution is subjected to sterile filtration and introduced aseptically into presterilized bottles, which are closed with sterilized rubber caps. Each bottle contains 5 ml of solution.

EXAMPLE 7

The result with the dipotassium salt of 2-n-butyl-1-[(2'-n-propylaminocarbonyl-aminosulfonylbphenyl-4-yl)methyl]- 4-methylthio-imidazole-5-carboxylic acid is described

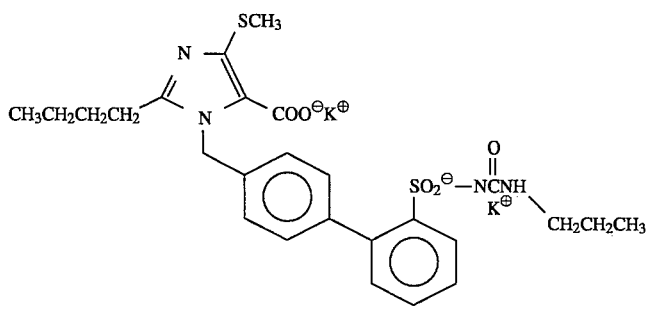

(XXII)

The action of the AT₁ angiotensin II receptor antagonist dipotassium salt of 2-n-butyl-1-[(2'-n-propylaminocarbonylaminosulfonyl-biphenyl- 4-yl)methyl]-4-methylthio-imidazole-5-carboxylic acid (Formula XXII) on post-ischemic reperfusion arrhythmias in the isolated, working rat heart was investigated using the method described in Example 1.

Result of the experiment:

Untreated control hearts fibrillate for 16.3 ±3 minutes during a reperfusion period of 30 minutes. The fibrillation incidence is 8 out of 8 hearts (8/8). The rat hearts which had been perfused with the compound of the formula (XXII) fibrillate for 5.37 ±1.2 minutes with an incidence of 4 out of 6 hearts (4/6).

This significant reduction in the ventricular fibrillation rate and the changed fibrillation incidence in isolated ischemic rat hearts demonstrate the protective action of the compound of the formula (XXII) in respect of post-ischemic reperfusion arrhythmias.

Examples 8 to 12 indicate the use forms for the treatment of disturbances in cardiac rhythm by the method according to the invention.

EXAMPLE 8

Preparation of a composition for oral use in the treatment of disturbances in cardiac rhythm.

1000 tablets, each of which comprises 20 mg of the potassium salt of 2-n-butyl-1-[(2'-n-propylaminocarbonylaminosulfonyl-biphenyl- 4-yl )methyl]-4-methylthio-imidazole- 5-carboxylic acid, are prepared using the following auxiliaries.

| | |
|---|---|
| Dipotassium salt of 2-n-butyl-1-[(2'-n-propylaminocarbonylaminosulfonyl-biphenyl-4-yl)methyl]-4-methylthio-imidazole-5-carboxylic acid | 20.0 g |
| Maize starch | 140.0 g |
| Gelatin | 7.5 g |
| Microcrystalline cellulose | 2.5 g |
| Magnesium stearate | 2.5 g |

The dipotassium salt of 2-n-butyl-1-[(2'-n-propylaminocarbonylaminosulfonyl-biphenyl- 4-yl)methyl]-4-methylthio-imidazole- 5-carboxylic acid and maize starch are mixed with an aqueous gelatin solution. The mixture is dried and ground to granules. The microcrystalline cellulose and magnesium stearate are mixed with the granules. The resulting granules are pressed to 1000 tablets, each tablet comprising 20 mg of the angiotensin II receptor antagonist. These tablets can be used for the treatment of disturbances in cardiac rhythm.

EXAMPLE 9

Analogously to Example 7, 1000 tablets, each of which contains 3 mg of 2-n-butyl-1-[(2'-n-propylaminocarbonylaminosulfonyl-biphenyl- 4-yl )methyl]-4-methylthio-imidazole- 5-carboxylic acid, are prepared by using 3 g of this compound in the mixture described in Example 2.

EXAMPLE 10

Gelatin capsules, each of which contains 20 mg of the potassium salt of 2-n-butyl-1-[(2'-n-propylaminocarbonylaminosulfonyl-biphenyl- 4-yl)methyl]-4-methylthio-imidazole- 5-carboxylic acid, are filled with the following mixture:

| | |
|---|---|
| Dipotassium salt of 2-n-butyl-1-[(2'-n-propylaminocarbonylaminosulfonyl-biphenyl-4-yl)methyl]-4-methylthio-imidazole-5-carboxylic acid | 20 mg |
| Potassium stearate | 1 mg |
| Lactose | 214 mg |

These capsules can be used for the treatment of disturbances in cardiac rhythm.

EXAMPLE 11

Analogously to Example 9, capsules, each of which contains 3 mg of of the dipotassium salt of 2-n-butyl-1-[ (2'-n-propylaminocarbonylaminosulfonyl-biphenyl-4-yl)methyl]- 4-methylthio-imidazole-5-carboxylic acid, are prepared using 3 mg of active compound.

EXAMPLE 12

The preparation of an injection solution for the treatment of disturbances in cardiac rhythm is described below:

| | |
|---|---|
| Dipotassium salt of 2-n-butyl-1-[(2'-n-propylaminocarbonylaminosulfonyl-biphenyl-4-yl)methyl]-4-methylthio-imidazole-5-carboxylic acid | 1 g |
| Methylparaben | 5 g |
| Propylparaben | 1 g |
| Sodium chloride | 25 g |
| Water for injections | 5 l |

The dipotassium salt of 2-n-butyl-1-[(2'-n-propylaminocarbonylaminosulfonyl-biphenyl- 4-yl)methyl]-4-methylthio-imidazole- 5-carboxylic acid, the preservatives and the sodium chloride are dissolved in 3 l of water for injections and the solution is made up to 5 l with water for injections. The solution is subjected to sterile filtration and introduced aseptically into presterilized bottles, which are closed with sterilized rubber caps. Each bottle contains 5 ml of solution.

EXAMPLE 13

The result with 5,7-dimethyl-2-ethyl-3-[(2'-tetrazol-biphenyl- 4-yl)methyl]imidazo[4,5-b]pyridine is described

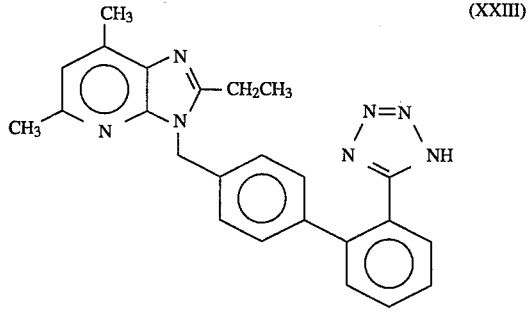

(XXIII)

The action of the $AT_1$ angiotensin II receptor antagonist dipotassium salt of 2-n-butyl-1-[(2'-n-propylaminocarbonylaminosulfonyl-biphenyl- 4-yl)methyl]-4-methylthio-imidazole- 5-carboxylic acid (Formula XXIII) on post-ischemic reperfusion arrhythmias in the isolated, working rat heart was investigated using the method described in Example 1.

Result of the experiment:

Untreated control hearts fibrillate for 16.3 ±3 minutes during a reperfusion period of 30 minutes. The fibrillation incidence is 8 out of 8 hearts (8/8). The rat hearts which had been perfused with the compound of the formula (XXIII) fibrillate for 9.2 ±3.1 minutes with an incidence of 5 out of 6 hearts (5/6).

This significant reduction in the ventricular fibrillation rate and the changed fibrillation incidence in isolated ischemic rat hearts demonstrate the protective action of the compound of the formula (XXIII) in respect of post-ischemic reperfusion arrhythmias.

Examples 14 to 18 indicate the use forms for the treatment of disturbances in cardiac rhythm by the method according to the invention.

EXAMPLE 14

Preparation of a composition for oral use in the treatment of disturbances in cardiac rhythm.

1000 tablets, each of which comprises 20 mg of 5,7-dimethyl- 2-ethyl-3-[(2'-tetrazol-biphenyl-4-yl)methyl]imidazo[ 4,5-b]pyridine, are prepared using the following auxiliaries.

| | |
|---|---|
| 5,7-Dimethyl-2-ethyl-3-[(2'-tetrazol-biphenyl-4-yl)-methyl]-imidazo[4,5-b]pyridine | 20.0 g |
| Maize starch | 140.0 g |
| Gelatin | 7.5 g |
| Microcrystalline cellulose | 2.5 g |
| Magnesium stearate | 2.5 g |

5,7-Dimethyl-2-ethyl-3-[(2'-tetrazol-biphenyl-4-yl)methyl] -imidazo[4,5-b]pyridine and maize starch are mixed with an aqueous gelatin solution. The mixture is dried and ground to granules. The microcrystalline cellulose and magnesium stearate are mixed with the granules. The resulting granules are pressed to 1000 tablets, each tablet comprising 20 mg of the angiotensin II receptor antagonist. These tablets can be used for the treatment of disturbances in cardiac rhythm.

EXAMPLE 15

Analogously to Example 1, 1000 tablets, each of which contains 3 mg of 5,7-dimethyl-2-ethyl-3-[(2' -tetrazol-biphenyl- 4-yl)methyl]-imidazo[4,5-b]pyridine, are prepared by using 3 g of this compound in the mixture described in Example 1.

EXAMPLE 16

Gelatin capsules, each of which contains 20 mg of 5,7-dimethyl- 2-ethyl-3-[(2'-tetrazol-biphenyl-4-yl)methyl]imidazo[ 4,5-b]pyridine, are filled with the following mixture:

| | |
|---|---|
| 5,7-Dimethyl-2-ethyl-3-[(2'-tetrazol-biphenyl-4-yl)methyl]imidazo[4,5-b]pyridine | 20 mg |
| Potassium stearate | 1 mg |
| Lactose | 214 mg |

These capsules can be used for the treatment of disturbances in cardiac rhythm.

EXAMPLE 17

Analogously to Example 4, capsules, each of which contains 3 mg of of the dipotassium salt of 5,7-dimethyl-2-ethyl- 3-[(2'-tetra-biphenyl-4-yl )-methyl]-imidazo[4,5-b] pyridine, are prepared using 3 mg of active compound.

EXAMPLE 18

The preparation of an injection solution for the treatment of disturbances in cardiac rhythm is described below:

| | |
|---|---|
| 5,7-Dimethyl-2-ethyl-3-[(2'-tetrazol-biphenyl-4-yl)methyl]-imidazo[4,5-b]pyridine | 1 g |
| Methylparaben | 5 g |
| Propylparaben | 1 g |
| Sodium chloride | 25 g |
| Water for injections | 5 l |

5,7-Dimethyl-2-ethyl-3-[(2'-tetrazol-biphenyl-4-yl)methyl] -imidazo[4,5-b]pyridine, the preservatives and the sodium chloride are dissolved in 3 l of water for injections and the solution is made up to 5 l with water for injections. The solution is subjected to sterile filtration and introduced aseptically into presterilized bottles, which are closed with sterilized rubber caps. Each bottle contains 5 ml of solution.

EXAMPLE 19

Tablets which can be used for the treatment of disturbances in cardiac rhythm are prepared as described in Example 2, except that instead of 2-n-propyl-1-[(2'-n-propylaminocarbonylaminosulfonyl-biphenyl- 4-yl)methyl]-4-methylthio-imidazole- 5-carboxylic acid, the following compounds are employed:

ethyl 2-n-propyl-1-[(2'-n-propylaminocarbonylaminosulfonyl-biphenyl- 4-yl)methyl]-4-methylthio-imidazole-5-carboxylate or ethyl 2-n-butyl-1-[(2'-n-propylaminocarbonylaminosulfonyl-biphenyl- 4-yl)methyl]-4-methylthio-imidazole-5-carboxylate, 3-[(2'-allylaminocarbonylaminosulfonyl-biphenyl-4-yl)methyl] -2-ethyl-7-methyl-imidazo[4,5-b]pyridine, 5,7-dimethyl-3-[(2'-methoxycarbonylaminosulfonyl-biphenyl- 4-yl)methyl]-2-ethyl-imidazo[4,5-b]pyridine, 2-n-butyl-4-chloro-5-hydroxymethyl-1-[(2'-(1H-tetrazol-5-yl)-biphenyl- 4-yl)methyl]-imidazole, 2-n-butyl-4-chloro-1-[(2'-(1H-tetrazol-5-yl)-biphenyl-4-yl)-methyl]-imidazole- 5-carboxylic acid (cf. P. C. Wong et al., J. Pharmacol. Exp. Theor. 252, 711 to 718, 1990) or the corresponding mono- or dipotassium salts of the stated compounds.

EXAMPLE 20

An injection solution is prepared analogously to the instructions described in Example 6, except that instead of 2-n-propyl-1-[(2'-n-propylaminocarbonylaminosulfonyl-biphenyl-4-yl)methyl]-4-methylthio-imidazole-5-carboxylic acid, the following substances are employed:

ethyl 2-n-propyl-1-[(2'-n-propylaminocarbonylaminosulfonyl-biphenyl- 4-yl)methyl]-4-methylthio-imidazole-5-carboxylate, ethyl 2-n-butyl-1-[(2'-n-propylaminocarbonylaminosulfonyl-biphenyl- 4-yl)methyl]-4-methylthio-imidazole-5-carboxylate, 3-[(2'-allylaminocarbonylaminosulfonyl-biphenyl-4-yl)methyl]- 2-ethyl-7-methyl-imidazo[4,5-b]pyridine, 5,7-dimethyl-3-[(2'-methoxycarbonylaminosulfonyl-biphenyl- 4-yl)methyl]-2-ethyl-imidazo[4,5-b]pyridine, 2-n-butyl-4-chloro-5-hydroxymethyl-1-[(2'-(1H-tetrazol-5-yl)-biphenyl- 4-yl)methyl]-imidazole, 2-n-butyl-4-chloro-1-[(2'-(1H-tetrazol-5-yl)-biphenyl-4-yl)methyl]-imidazol- 5-carboxylic acid (cf. P. C. Wong et al., J. Pharmacol. Exp. Theor. 252, 711–718, 1990) or corresponding mono- or dipotassium salts thereof.

We claim:

1. A method for the treatment of disturbances in cardiac rhythm in a mammal comprising the step of administering to a mammal in recognized need thereof an effective amount of an antagonist for angiotensin II receptors of the $AT_1$ subtype having the formula (I)

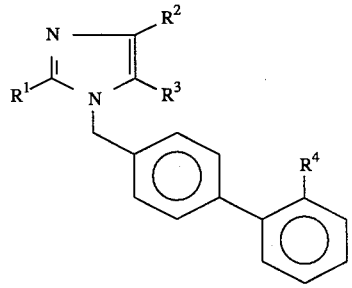

(I)

in which $R^1$ is $(C_1-C_7)$-alkyl, $(C_3-C_7)$-alkenyl or $(C_3-C_7)$-alkylnyl, $R^2$ is Cl or —S(O)$_r$—R$^{19}$;

$R^3$ is —CH$_2$OR$^5$ or —CO—R$^6$;

$R^4$ is —SO$_2$—NH—CO—NR$^7$R$^9$, —SO$_2$—NH—CO—OR$^7$, —SO$_2$—NH—CO—R$^7$, —SO$_2$—N=CH—N(CH$_3$)$_2$ or tetrazoyl;

$R^5$ is hydrogen;

$R^6$ is hydrogen or OR$^7$;

$R^7$ and $R^9$ are identical or different and are hydrogen, $(C_1-C_6)$-alkyl, $(C_3-C_8)$-cycloalkyl, $(C_3-C_6)$-cycloalkyl-$(C_1-C_3)$-alkyl, $(C_6-C_{12})$-aryl, $(C_6-C_{10})$-aryl-$(C_1-C_4)$-alkyl, $(C_2-C_6)$-alkenyl, $(C_3-C_6)$-alkenoyl or $(C_3-C_6)$-alkynyl;

$R^{19}$ is $(C_1-C_8)$-alkyl; and r is 0, 1 or 2;

or a physiologically tolerable salt thereof.

2. The method as claimed in claim 1, in which $R^1$ is $(C_1-C_7)$-alkyl;

$R^2$ is —S—$(C_1-C_4)$-alkyl;

$R^3$ is —CO—R$^6$;

$R^4$ is —SO$_2$—NH—CO—NHR$^9$ or —SO$_2$—NH—CO—OR$^7$;

$R^6$ is hydrogen or OR$^7$;

$R^7$ and $R^9$ are identical or different and are hydrogen, $(C_1-C_6)$-alkyl, $(C_3-C_8)$-cycloalkyl, $(C_3-C_6)$-cycloalkyl-$(C_1-C_3)$-alkyl, $(C_6-C_{12})$-aryl, $(C_6-C_{10})$-aryl-$(C_1-C_4)$-alkyl, $(C_2-C_6)$-alkenyl, $(C_3-C_6)$-alkenoyl or $(C_3-C_6)$-alkynyl;

or a physiologically tolerable salt thereof.

3. The method as claimed in claim 2, in which $R^1$ is $(C_1-C_7)$-alkyl;

$R^2$ is —S—$(C_1-C_4)$-alkyl;

$R^3$ is —CO—R$^6$;

$R^4$ is —SO$_2$—NH—CO—NHR$^9$ or —SO$_2$—NH—CO—OR$^7$;

$R^6$ is hydrogen or OR$^7$;

$R^7$ and $R^9$ are identical or different and are hydrogen or $(C_1-C_4)$-alkyl;

or a physiologically tolerable salt thereof.

4. A method for the treatment of disturbances in cardiac rhythm in a mammal comprising the step of administering to a mammal in recognized need thereof an effective amount of an antagonist for angiotensin II receptors of the $AT_1$ subtype having the formula (II)

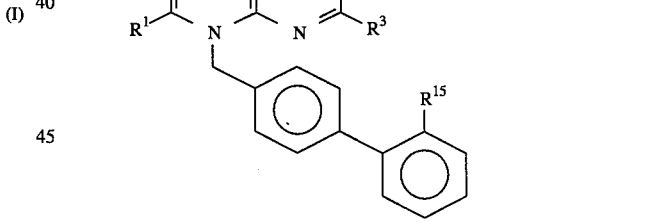

(II)

in which $R^1$ is $(C_1-C_7)$-alkyl, $(C_3-C_7)$-alkenyl or $(C_3-C_7)$-alkylnyl;

$R^2$ and $R^3$ are identical or different and are hydrogen or $(C_1-C_4)$-alkyl;

$R^{15}$ is —SO—NR$^{18}$—CO—OR$^{17}$, —SO$_2$—NR$^{18}$—CO—NHR$^{16}$, —SO$_2$—NH—CO—R$^{17}$ or tetrazoyl;

$R^{16}$ and $R^{17}$ are identical and are $(C_1-C_4)$-alkyl, $(C_2-C_6)$-alkenyl, $(C_3-C_8)$-cycloalkyl-$(C_1-C_4)$-alkyl, phenyl or phenyl-$(C_1-C_4)$-alkyl;

$R^{18}$ is hydrogen or $(C_1-C_6)$-alkyl;

or a physiologically tolerable salt thereof.

5. The method as claimed in claim 4, in which $R^1$ is $(C_1-C_4)$-alkyl;

$R^{15}$ is —SO—NR$^{18}$—CO—OR$^{17}$ or —SO$_2$—NR$^{18}$—CO—NHR$^{16}$;

$R^{16}$ and $R^{17}$ are identical and are $(C_1-C_4)$-alkyl, $(C_2-C_6)$- alkenyl or $(C_3-C_8)$-cycloalkyl-$(C_1-C_4)$-alkyl;
$R^{18}$ is hydrogen;
or a physiologically tolerable salt thereof.
6. The method as claimed in claim 5, in which $R^{15}$ is $-SO_2-NH-CO-NHR^{16}$;
or a physiologically tolerable salt thereof.

* * * * *